United States Patent
Pi et al.

(10) Patent No.: US 6,194,726 B1
(45) Date of Patent: Feb. 27, 2001

(54) SEMICONDUCTOR RADIATION DETECTOR WITH DOWNCONVERSION ELEMENT

(75) Inventors: Bo Pi, San Diego; Timothy C. Collins, Carlsbad; Richard L. Conwell, Del Mar, all of CA (US)

(73) Assignee: Digirad Corporation, San Diego, CA (US)

(*) Notice: Subject to any disclaimer, the term of this patent is extended or adjusted under 35 U.S.C. 154(b) by 0 days.

(21) Appl. No.: 09/158,639

(22) Filed: Sep. 22, 1998

Related U.S. Application Data

(60) Continuation-in-part of application No. 08/887,960, filed on Jul. 3, 1997, now Pat. No. 5,847,396, which is a division of application No. 08/672,831, filed on Jun. 28, 1996, now Pat. No. 5,786,597, which is a continuation-in-part of application No. 08/372,807, filed on Dec. 23, 1994, now abandoned.
(60) Provisional application No. 60/098,227, filed on Aug. 28, 1998.

(51) Int. Cl.[7] ................................................. G01T 1/164
(52) U.S. Cl. .......................... 250/363.1; 250/370.11; 250/363.02; 250/363.06
(58) Field of Search ....................... 250/363.1, 370.11, 250/363.02, 363.06

(56) References Cited

U.S. PATENT DOCUMENTS

| | | | |
|---|---|---|---|
| 4,047,037 | * 9/1977 | Schlosser et al. ............... | 250/363.1 |
| 5,227,635 | 7/1993 | Iwanczyk . | |
| 5,391,882 | 2/1995 | Rhiger . | |
| 5,428,223 | * 6/1995 | Jatteau et al. ................... | 250/363.06 |
| 5,448,073 | * 9/1995 | Jeanguillaume ................ | 250/363.02 |
| 5,596,198 | * 1/1997 | Perez-Mendez ................ | 250/370.11 |
| 5,773,829 | 6/1998 | Iwanczyk et al. . | |
| 5,777,338 | 7/1998 | He . | |
| 5,786,597 | 7/1998 | Lingren et al. . | |
| 5,823,865 | 10/1998 | Trissel et al. . | |

OTHER PUBLICATIONS

He, et al., "1–D Position Sensitive Single Carrier Semiconductor Detectors", Nuclear Instruments and Methods in Physics Research, A 380 (1996) 228–231.

He, "Potential Distribution Within Semiconductor Detectors Using Coplanar Electrodes", Nuclear Instruments and Method in Physics Research, A 365 (1995) 572–575.

* cited by examiner

Primary Examiner—Constantine Hannaher
Assistant Examiner—Otilia Gabor
(74) Attorney, Agent, or Firm—Fish & Richardson PC

(57) ABSTRACT

A radiation detection device for gamma radiation is disclosed having an array of crystals optically positioned adjacent an optional collimator, the crystals emitting visible light upon illumination by the incident gamma radiation. An array of photodetectors is optically positioned adjacent the crystal array on the side of the crystal array opposite that of the collimator. A select photodetector in the photodetector array provides an output signal when the select photodetector is illuminated by the visible light. An integrated circuit having an input from the output signals of said array of photodetectors is used to process and output signals indicative of the intensity and position of the gamma radiation.

27 Claims, 15 Drawing Sheets

MODULE BOARD BLOCK DIAGRAM

CSI CRYSTALS

SILICON PHOTO-DIODE ARRAY

MCM MODULE AND ASIC

SEMICONDUCTOR RADIATION DETECTOR WITH DOWNCONVERSION ELEMENT

CROSS-REFERENCE TO RELATED APPLICATIONS

This application is a continuation-in-part of co-pending U.S. patent application Ser. No. 08/887,960, entitled "Semiconductor Gamma-Ray Camera and Medical Imaging System", filed Jul. 3, 1997, now U.S. Pat. No. 5,847,396 which is a divisional of U.S. patent application Ser. No. 08/672,831, filed Jun. 28, 1996, now U.S. Pat. No. 5.786,597 which is a continuation-in-part of U.S. patent application Ser. No. 08/372,807, entitled "Semiconductor Gamma-Ray Camera and Medical Imaging System", filed Dec. 23, 1994, now abandoned. This application also claims benefit of U.S. Provisional application No. 60/098,227, filed Aug. 28, 1998, now expired.

BACKGROUND

1. Field of the Invention

This invention relates to a device for detecting ionizing radiation, and more particularly to semiconductor radiation detectors employing downconversion elements along with the active semiconductor element.

2. Description of Related Art

Medical diagnostic imaging began with the discovery of x-rays by W. C. Roentgen in 1895 and today includes radiography, nuclear medicine imaging, ultrasound imaging, computed tomographic imaging, and magnetic resonance imaging. In general the goal of each type of medical imaging is to provide a spatial mapping of a parameter, feature, or process within a patient.

In radiology and computed tomography, a source of x-rays is beamed through the patient onto a suitable detector such as a film or a plate. The detector measures the intensity distribution of the incident beam of x-rays and provides an image representing the attenuation of the radiation resulting from the absorption and scattering within the patient's body.

Nuclear medicine involves injection of a radiopharmaceutical into a patient and measurement of the intensity distribution of gamma radiation emitted from the patient's body. Radiopharmaceuticals are formed by attaching a radioactive tracer to a pharmaceutical that is known to preferentially accumulate in the organ of interest. Thus, the radiation pattern is a measure of blood flow, metabolism, or receptor density within the organ of interest and provides information about the function of the organ. Either a single projection image of the radiation pattern may be taken (planar imaging) or many projection images may be acquired from different directions and used to compute the three dimensional emission distribution (single photon emission computed tomography, or "SPECT"). Radiation-imaging systems used in nuclear medicine are often referred to as "gamma" cameras.

Pioneer nuclear medicine imaging systems used scanning methods to generate images. Such pioneer systems generally used a scintillation-type gamma-ray detector equipped with a focusing collimator which moved continuously in selected coordinate directions, i.e., in a series of parallel sweeps, to scan regions of interest. A disadvantage of these early imaging systems was the lengthy exposure times that were required to derive an image of the system or organ under test. In addition, dynamic studies of such organs were often difficult to obtain.

Another type of prior art radiation detection system utilizes an "Anger" type gamma scintillation camera (named after its inventor H. O. Anger, see "A New Instrument for Mapping Gamma Ray Emitters," *Biology and Medicine Quarterly Report,* U.C.R.L.-3653, 1957), for determining the radiation pattern emitted from a patient's body. These nuclear medicine imagers use large sodium iodide scintillating crystals in conjunction with a bank of photomultiplier tubes (PMTs). A collimating aperture in front of the scintillation crystal focuses the gamma rays on the crystal, and gamma rays from a radiopharmaceutical injected into the patient produce light flashes (scintillations) in the crystal which are converted into electrical signals by the PMTs. High density shielding material, typically lead, is used to cover the sides and back of the radiation detection assembly to prevent radiation from entering the detector by any path other than through the collimator. A computer locates each flash from the relative magnitudes of the PMT signals. The crystals used are typically 200 to 400 square inches in area.

Limitations in the Anger camera stem from the process of converting scintillations into electrical signals. Sources of distortion include: 1) variation of the acceptance field-of-view angle of the PM tubes with distance from the scintillation event, 2) refraction and light guiding due to index of refraction mismatches, 3) unavoidable dead regions between PMTs, 4) higher effective density (hence, heavier weighting) of distant PMTs, 5) non-uniform spatial response of individual PMTs, 6) variation in response from one PMT to another, 7) temporal variation of PMT response, and 8) an unavoidable dead margin several centimeters wide around the perimeter related to the inability of determining positions outside the middle of the outer PMTs. Other errors stem from instabilities in the PMTs and the fragility and hygroscopic nature of the scintillation crystal.

Disadvantageously, because of the large size of the detection assembly that results from the combination of scintillator, light pipe, and photomultiplier tubes, the lead shielding dramatically increases the weight and cost of Anger cameras. Furthermore, the non-sensitive (dead) margin around the perimeter of the Anger camera makes it difficult to adequately image small organs and some body parts (the breast, for example). In addition, the large size of the Anger camera and its weight prevent it from being used effectively in locations such as in operating rooms, intensive care units, or at the patient's bedside.

Semiconductor detector-array imagers have been proposed for solving problems with Anger cameras, e.g., see U.S. Pat. Nos. 4,292,645; 5,132,542; IEEE Transactions on Nuclear Science, vol. NS-27, No. 3, June 1980, "Semiconductor Gamma Cameras in Nuclear Medicine"; and IEEE Transactions on Nuclear Science, Vol. NS-25, No. 1, February 1978, "Two-Detector, 512-Element, High Purity Germanium Camera Prototype." It has long been recognized that semiconductor detector arrays are potentially attractive for nuclear medicine imaging because of their very small size and weight, excellent spatial resolution, direct conversion of gamma photons into electrical signals, capability of on-board signal processing, high stability, and reliability. Using this technique, gamma-ray radiation absorbed in a semiconductor detector produces holes and electrons within the detector material which, due to the influence of a bias voltage, separate and move toward opposite surfaces of the semiconductor material in accordance with their respective electrical charge polarities. The electron and hole currents are then amplified and conditioned by electronic circuitry to produce electrical signals which are processed to indicate the location and intensity of the corresponding incident gamma-ray radiation.

Prototype semiconductor detector-array cameras embodying these principles have been developed with varying degrees of success. For example, attempts at using two-dimensional detector arrays of cryogenically-cooled-germanium detectors and room-temperature $HgI_2$ detectors have generally been limited to the scientific laboratory due to the problems associated with cryogenic cooling and practical difficulties with $HgI_2$ technology. An early feasibility study of an imaging system based on a rotating linear array of cadmium telluride (CdTe) detectors has similarly not proven to be a satisfactory solution and has apparently been abandoned.

One example of a prior art semiconductor gamma camera is described in U.S. Pat. No. 4,292,645, to Schlosser, et al. Schlosser teaches an improved technique for providing the necessary electrical contact to doped regions of a semiconductor gamma detector principally comprised of germanium. A layer of resistive material makes contact with conductive strips on the detector surface, and two readout contacts at the sides of the resistive layer, parallel to the strips and connected to two amplifiers, allow identification of the strip where a gamma ray is absorbed. The opposite side of the detector is arranged the same except that the strips are orthogonal to those on the top. The spatial position of an event is the intersection of the identified orthogonal strips. Two amplifiers for the top surface and two amplifiers for the bottom surface handle all events in the entire imager. Though this keeps the electronic component count small, it is a disadvantage to use the entire crystal for detection of each gamma ray. As a result of this, the resolution gets worse and the achievable count rate decreases as the size of the detector is increased.

Another example of a prior-art gamma-ray-imaging system using a semiconductor detector array is described in Materials Research Society Symposium Proceedings, vol. 302 (Materials Research Society, Pittsburgh, 1993), pp. 43–54, "Multi-Element Mercury Iodide Detector Systems for X-Ray and Gamma-Ray Imaging," by Bradley E. Patt. Patt teaches the use of orthogonal strips on opposite sides of the semiconductor crystal to define the semiconductor detector array pixels, with one amplifier being used for each strip. The coincidence of signals from orthogonal strips is used to define the position at which a gamma ray is absorbed within the crystal. Disadvantageously, as the area of the detector gets larger and the length of the strips increases, the capacitance associated with the strip and the leakage current in the strip from the detector increase. Both capacitance and leakage current reduce the pulse energy resolution which degrades the imager performance.

The prior art lacks a semiconductor detector array that is large enough to satisfy nuclear medicine applications or that operates at room temperature. Therefore, there is a need for a detector which overcomes the disadvantages of the Anger camera, has an active area appropriate for medical imaging application, has negligible dead region around the perimeter, and operates at room temperature. There is a need for a cost-effective means of manufacturing such detectors for nuclear medicine and other applications.

A semiconductor detector array may be realized by combining together many individual detector elements. However, when the individual detector elements are made sufficiently small to meet spatial resolution requirements, the number of amplifiers needed to amplify the signals becomes very large. For infrared and low-energy x-ray applications, prior art focal-plane arrays and silicon-strip detectors combine amplifiers for each element and a multiplexer that provides a single output for the large number of inputs (see Nuclear Instruments and Methods in Physics Research, Vol. 226, 1984, pp. 200–203; and IEEE transactions on Nuclear Science, Vol. NS-32, No. 1, February 1985, p 417). These prior art readout circuits are not adequate for handling signals produced by gamma-ray detectors such as the detector arrays required for nuclear medical imaging.

Current detector arrays commonly employ Cadmium-Zinc-Telluride (CdZnTe) ("CZT") as a radiation detector element. CZT elements may detect a broad band of radiation and are thus advantageous. On the other hand, CZT elements are sometimes fragile and may be damaged when installed in an imaging array mother board or if the element's module must be removed for repair or replacement. In addition, CZT is prone to being affected by moisture or airborne vapor that may affect the insulative characteristics of the surface of the semiconductor. Furthermore, special electronics may be required to operate and receive signal data from CZT detectors. Despite such drawbacks, CZT has been a common semiconductor material for use in such systems.

Thus, there is a need for a system which does not have the drawbacks of CZT elements, or alternatively can accommodate such drawbacks, but which may still be used to achieve all-side buttability. There is further a need for such a system which employs pre-existing photodetectors and electronics, without substantial modification.

Moreover, the prior art lacks a semiconductor detector array that is large enough to satisfy nuclear medicine applications or that operates at room temperature. Therefore, the inventors have determined that there is a need for a detector which overcomes the disadvantages of the Anger camera, has an active area appropriate for medical imaging application, has negligible dead region around the perimeter, and operates at room temperature. There is a further a need for a cost-effective means of manufacturing such detectors for nuclear medicine and other applications.

SUMMARY

The present invention provides such a semiconductor gamma-ray camera and imaging system. One embodiment of the invention provides a semiconductor detector employing a downconversion scintillator element, such as CsI, to extend the detector range and sensitivity. Another embodiment of the imaging system includes downconversion element, such as CsI, and conventional photodetector elements for sensing radiation emitted from a subject under test. The detector may be connected to conventional photodetector arrays and electronics for conditioning and processing the detected radiation signals.

More particularly, in one embodiment the imaging system includes an imaging head, a signal processor, a data acquisition system and an image processing computer. The imaging head preferably includes an x-ray or gamma-ray detector and an entrance aperture such as a collimator or pinhole for directing the rays to the detector. In the preferred embodiment, the detector comprises a plurality of closely-packed detection modules. Each detection module comprises a plurality of detection elements mounted to a housing unit. The detection elements produce electrical pulses having amplitudes indicative of the magnitude of radiation absorbed by the detection elements. The detection elements are coupled to electronics contained within the imaging head. The electronics includes circuitry for conditioning and processing the signals generated by the detection elements and for preparing the processed signals for further processing by the signal processor. Each detection element has a corresponding conditioning and processing channel.

Each conditioning and processing channel stores the amplitudes of the detection element electrical pulses which exceed a predetermined threshold. When a detection element absorbs sufficient radiation to produce an electrical pulse having an amplitude which exceeds the threshold, the channel associated with the detection element records a valid detection element "event". The detection modules employ a fall-through circuit which automatically finds only those detection elements that have recorded a valid hit. When prompted by the signal processor, the fall-through circuit searches for the next detection element and associated channel having a valid event. Upon finding the next recorded event, the detection module produces the address of the element and the amplitude of the electrical pulse which produced the valid event. The address of each detection element and pulse amplitude is provided to the signal processor for further processing.

The signal processor acquires data from the conditioning and processing channels, normalizes and formats the data, and stores it in memory blocks for access by the data acquisition computer. In addition, the signal processor provides a bias voltage for the detector and provides the event threshold voltage that is used by the detection modules for discriminating valid events. The signal processor performs diagnostics, gain normalization, and response efficiency normalization functions.

The data acquisition system includes hardware and software which communicate with the signal processor and the image processing computer system. The data acquisition system controls acquisition and processing of data received from the conditioning and processing channels, produces image data based upon the event data in a format that is compatible with existing imaging cameras, and transmits the data to the image processing computer. The data acquisition system also provides a mechanism for maintaining detection element event histograms and pulse-height distribution data. The data acquisition system can produce images in a standard format to allow images to be displayed using commercially available imaging systems.

The image processing computer displays images based upon the signals generated by the detection elements. The image processing computer formulates images based upon the processed signals and displays the formulated images on a display device. The image processing computer provides an interface with an operator, controls data acquisition modes, receives image data from the data acquisition system, displays images in real time on a display device, and communicates with display and other readout devices. The image processing computer also provides a mechanism for adjusting operational parameters used within the imaging system.

Advantages of the invention include one or more of the following. The radiation detector lacks some of the drawbacks of CZT detectors. The detector is all-side buttable and significantly eliminates dead space between detector active areas. One embodiment of the detector structure may be used to supplement a CZT detector with a downconversion material, such as CsI, to greatly expand the sensitivity and range of the detector.

The details of the preferred embodiment of the invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention. The following description describes detection of gamma rays, however, the detection of x-rays can be equally considered. Many x-ray applications would require different dimensions of the sub-components.

Overview

Figure 1:
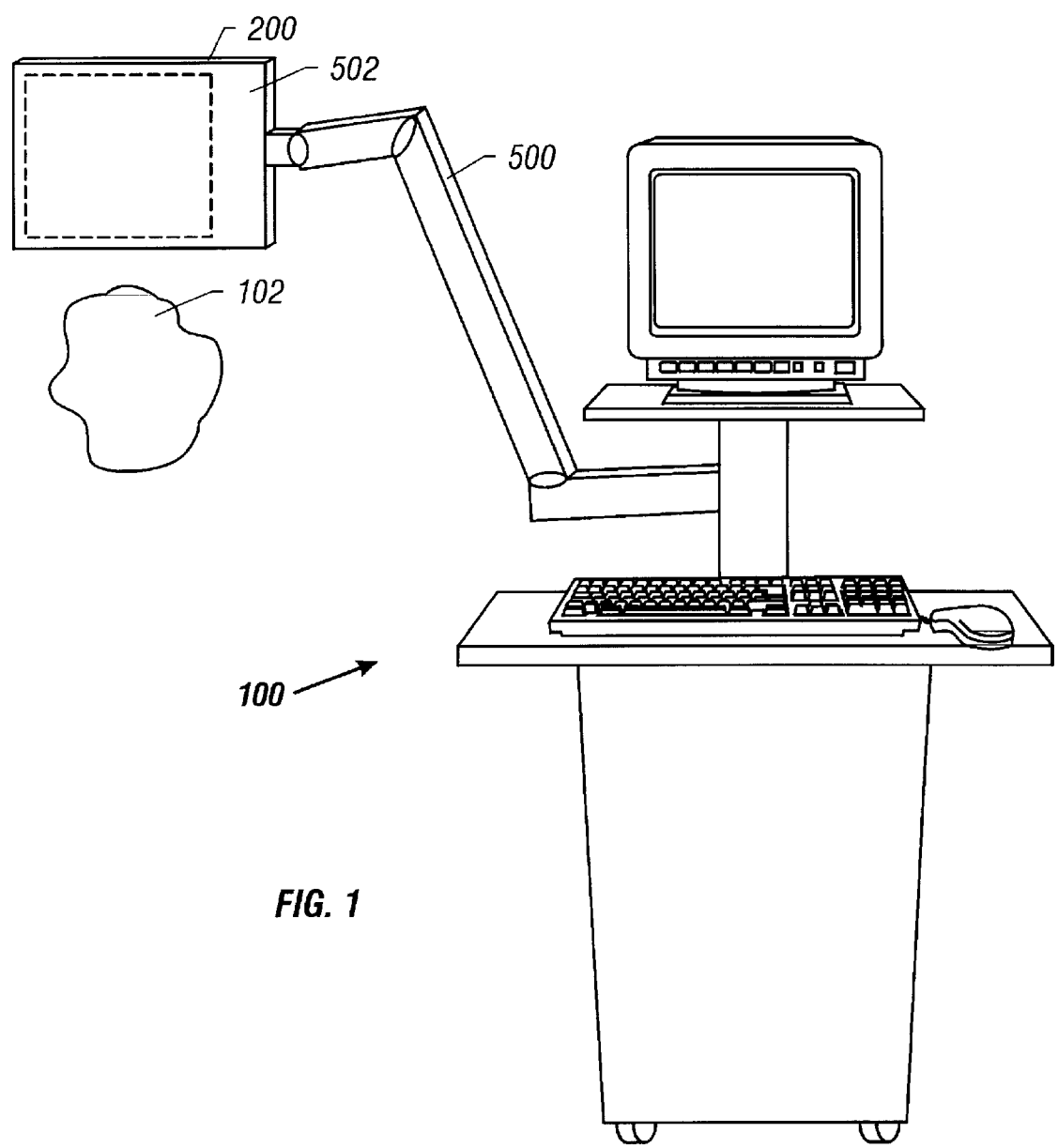
FIG. 1 shows the camera and imaging system of the present invention.
Figure 2:
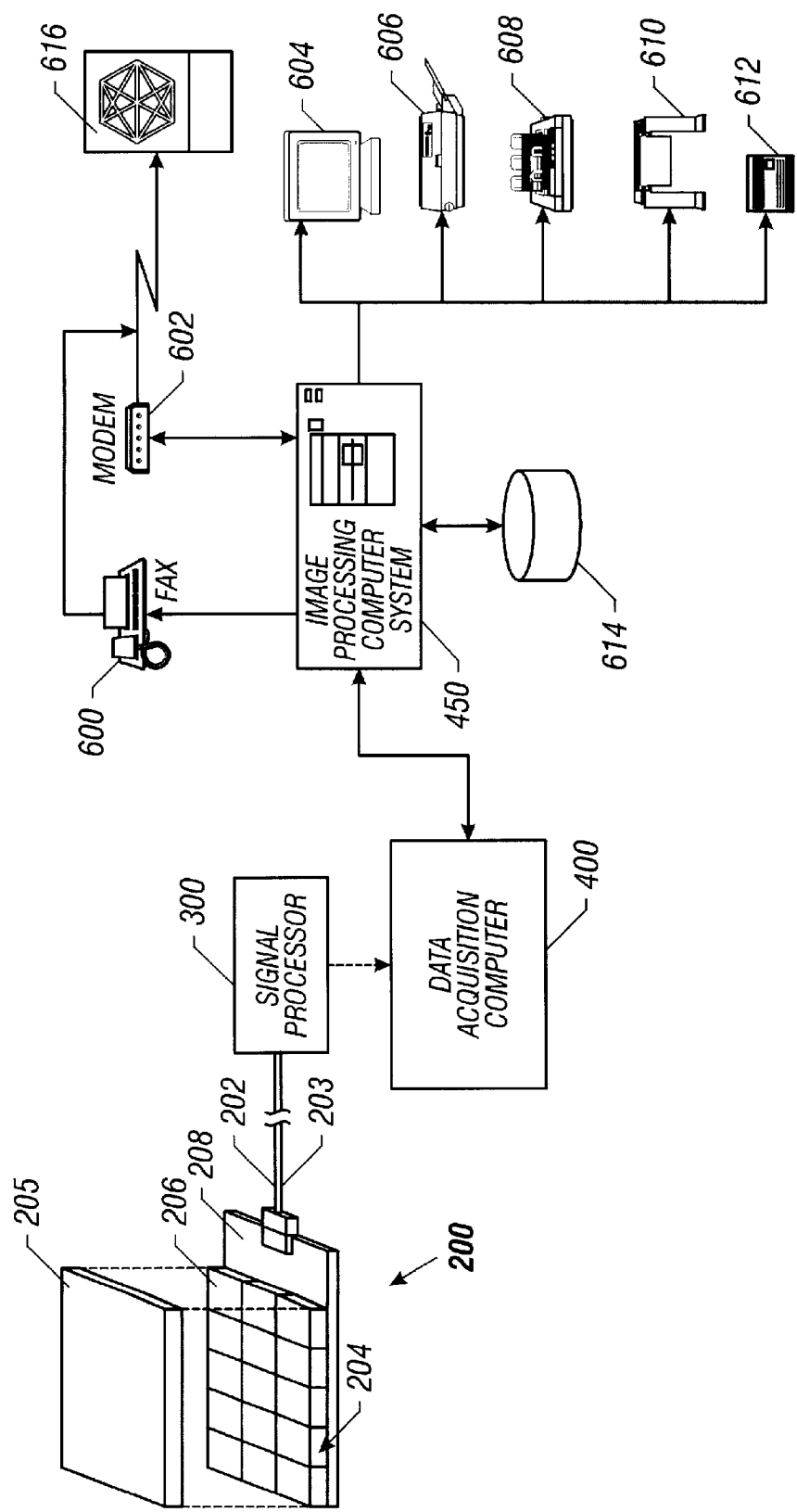
FIG. 2 shows the camera and imaging system of FIG. 1, showing the detector, signal processor, data acquisition system, and image processing computer system of the present invention.

The semiconductor-based gamma-ray camera and medical imaging system of the present invention, hereinafter referred to as a "camera," is shown in FIG. 1 and referred to by reference numeral 100. Referring simultaneously to FIGS. 1 and 2, the camera 100 of the present invention comprises a gamma-ray detector 200, an entrance aperture such as a collimator or pinhole (not shown in this figure) for directing the gamma rays to the detector, a signal processor 300, a data acquisition computer 400, an image processing computer system 450, and a gantry 500 for positioning the camera adjacent to a patient, an organ, or other object 102. The detector 200 is used to sense radiation emitted from the object 102. The signals generated by the detector 200 are transmitted to the signal processor 300 using any convenient means, preferably a digital communications link 202.

As shown in FIG. 2, the camera 100 also preferably includes a plurality of input/output devices for transmitting and displaying derived images of the object 102 to both on-site and remote users of the present invention. For example, the present camera 100 preferably includes, at a minimum, an input from a device such as an electrocardiograph and a display device 604 for displaying images of the object 102 to on-site users (not shown). However, images can also be transmitted to off-site or remote users via a telecommunications network 616 using a facsimile machine 600 or a modem 602 or direct digital network (not shown). The camera 100 can produce "hard copies" of images using a plurality of paper display devices. For example, the camera 100 can include a laser printer 606, a dot-matrix printer 608, and a plotter 610 for providing paper or film copies of an image. The camera 100 can also store digitized images of the object 102 in a magnetic data storage device 614 and/or an optical data storage device 612.

Both planar and single photon emission computed tomographic (SPECT) images of the emission of radiation from radioisotopes are obtainable using the present camera 100. The camera 100 is designed to provide images of areas that are difficult to access and image using conventional gamma cameras. The camera 100 is also designed to provide images that are conventionally obtained in nuclear medicine. As shown in FIG. 2, the gamma-ray detector 200 preferably comprises an array 204 of detection modules 206 mounted upon a module board 208. The module board 208 transmits the signals generated by the detection modules to the signal processor 300 for processing.

As described in more detail below with reference to FIGS. 3A–3B, each of the detection modules 206 includes an array of detection elements or pixels 212 which comprise semiconductor material that can detect gamma radiation with acceptable performance at room temperature. Each module, in a different embodiment, may further comprise a scintillation element of a downconversion material, such as CsI (FIG. 3C). In addition, each detection module 206 includes integrated circuits (ICs) in a carrier 214, operatively coupled to the detection elements 212, that amplify, condition, and process the electrical signals generated by the detection elements for transmission to the signal processor 300. The signal processor 300 acquires the signals from the gamma-ray detector 200, makes corrections to the data, and places the data into memory for use by the data acquisition computer 400 for forming images of the object 102. The images are displayed on the display 604 and stored, printed, or transmitted using the other output devices shown in FIG. 2, or such as solid state monitors. The significant components of the camera 100 are described below in respective subsections.

Gamma-Ray Detector

The gamma-ray detector 200 of the present invention comprises an array of closely-packed detection modules 206 mounted upon the module board 208. The module board 208 routes the signals generated by the detection modules 206 to the signal processor 300. The detector 200 preferably includes an 8×8 array of detection modules 206. For convenience of presentation, FIG. 2 shows a 4×5 array of detection modules 206. The detection modules 206 are preferably dimensioned 1-inch by 1-inch square. Therefore, the preferred embodiment of the gamma-ray detector 200 has an "active" sensing area of 64 square inches. This is sufficiently large to image most body organs or structures.

Another embodiment of the present invention mounts the detection modules 206 in a shape other than a plane to form a detection surface that is more appropriate for imaging some objects. Also, although the illustrated embodiments describe a detector 200 having detection modules 206 arranged in an array format, the present invention contemplates detectors 200 including detection modules 206 arranged in other configurations. For example, the modules 206 can be arranged linearly, in a circle, or in any other convenient configuration.

The module board 208 and the detection modules 206 of the detector 200 are housed within a light-tight housing. Shielding material, preferably lead, is positioned behind and on the sides of the module board 208 and detection modules 206 to prevent stray radiation from adversely affecting the acquired image. The shields are alternatively made of tungsten carbide or other high-density material and have sufficient mass to block unwanted stray radiation from reaching the detection elements and thereby degrading the quality of the images produced by the camera 100. The housing (not shown) also preferably includes a thin aluminum window which is positioned over the face of the detection modules 206. The window protects the detection modules from light and physical damage yet allows gamma rays emitted from the object 102 under test to penetrate the window and to be absorbed in the detection elements 212 such that they, in turn, radiate gamma rays. Alternatively, the window can be made from any low Z material which does not absorb an appreciable amount of the radiation being imaged.

The housing is secured around the module board 208, detection elements 206, and shielding material using screws or other attachment means. The digital communications link 202 enters the housing through a hole or slot (not shown) formed at one end. The slot and the housing edges are preferably made light-tight and may seal the modules from the environment. The housing is preferably supported to the gantry 500 using vibration isolation techniques. In one preferred embodiment, the temperature within the housing is controlled by a cooling system which removes heat from the housing.

The total thickness of the device may be less than about five inches thick for portability, and more preferably less than about two or three inches thick.

The dead region around the active surface at the detector is small. It is made up of the shielding material on the sides of the detector and the support housing, and it is typically less than 0.5 inch.

Detection Modules

First Embodiment

Figure 3A:
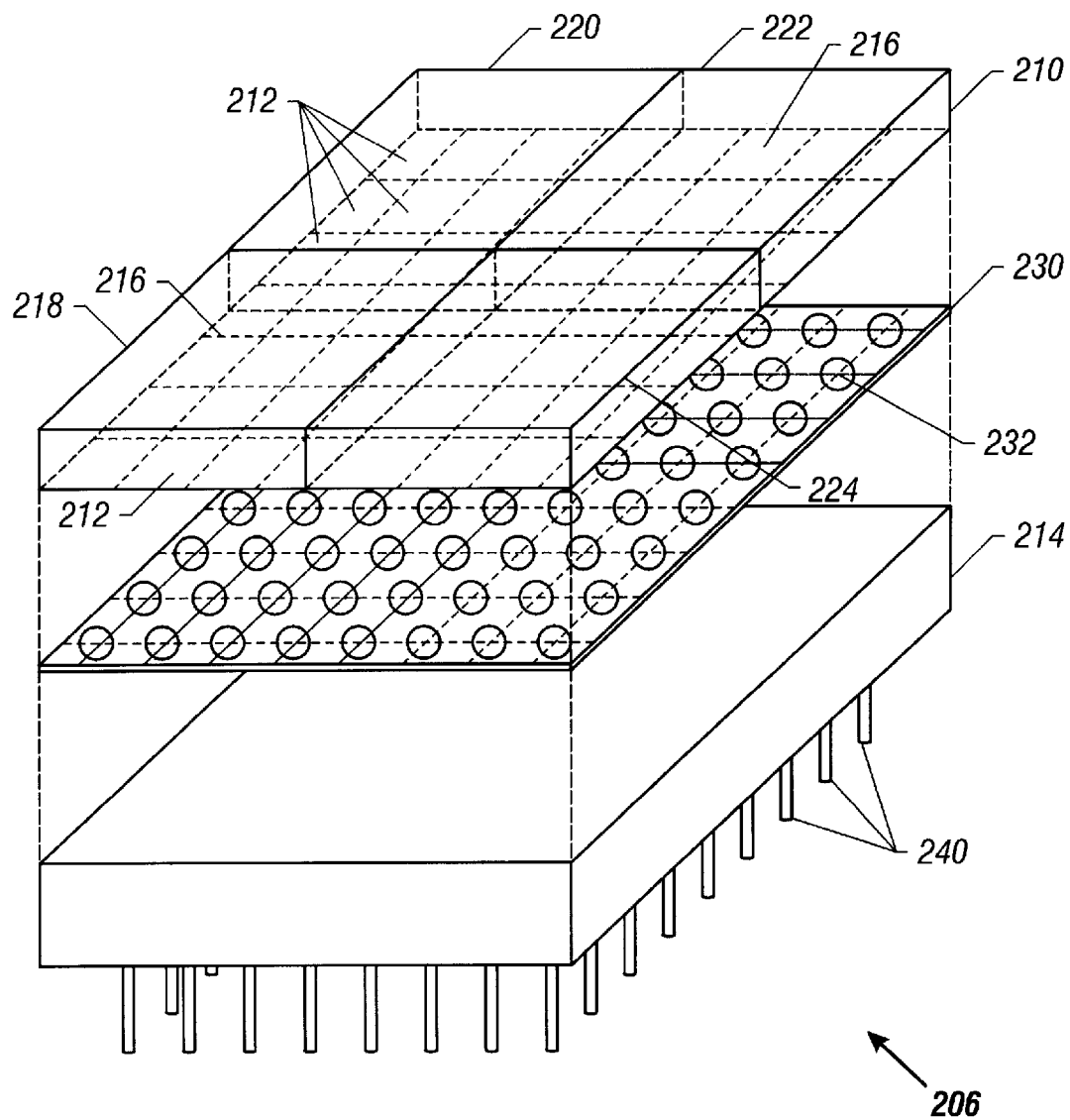
FIG. 3A shows an exploded perspective view of a detection module used in the detector shown in FIG. 2.

FIG. 3A shows an exploded perspective view of one detection module 206 of the present invention. As depicted in FIG. 3A, the detection module 206 includes an integrated circuit mounted within a 1-inch square ceramic or plastic carrier. The semiconductor detection material, subcomponent 210, of the detection module 206 includes an array of detection elements 212. The detection elements 212 are preferably configured in an 8×8 array. In the preferred embodiment of the present invention, the detection elements 212 comprise a plurality of cadmium-zinc-telluride (CZT) gamma-ray detection areas formed on the lower surface of sub-component 210. The crystals can alternatively comprise cadmium telluride, mercuric iodide, germanium, silicon, or other x-ray or gamma-ray sensitive materials. As is known in the art, CZT crystals provide good energy and spatial resolution, can operate at room temperature, and can be manufactured in large volumes in a variety of dimensions. The CZT crystals convert gamma rays received from an object under test 102 (FIG. 1) into electrical charge pulses. The amplitude of the electrical pulses are indicative of the energy of the gamma rays absorbed. CZT crystals are further advantageous in that they can detect a broad band of radiation. Such crystals and the electronics described herein may be used as a high quality semiconductor photodetector.

The detection modules 206 shown in FIG. 3A are assembled with thin plates positioned on both the top and bottom surfaces of the sub-component 210. The upper plate (not shown) provides a means for applying a bias voltage to the detection modules 206, insulates the bias voltage from the detector housing, and provides physical protection for the CZT crystals. The upper plate is designed to allow the gamma rays emitted from the object 102 to penetrate the plate and to be absorbed in the detection elements 212. In the preferred embodiment, the plates are made from 0.5 mm thick alumina. Alternatively, the upper and/or lower plates are made from glass epoxy circuit board or other insulating material. The alumina or other insulating layer narrows the detection band of the CZT to high energies. A lower plate 230 provides the means for connecting the detection elements 212 to the circuit carrier 214. The lower plate 230 includes a plurality of contact pads 232 which correspond in position to the positions of the detection elements 212. The plurality of contact pads 232 provide electrical connection for each detection element to a corresponding input contact pad on the top surface of the circuit carrier 214. The contact pads 232 are electrically isolated from each other.

The circuit carrier 214 houses the ICs and passive components, and provides interconnections from the ICs to the detection elements 212 and to the module board 300. The circuit carrier 214 preferably comprises ceramic, plastic, or various glass epoxies. In the preferred embodiment, thick-film resistors and capacitors in the circuit carrier 214 couple the signals from the detection elements 212 to the inputs of the ICs and shunt detector leakage current to ground.

In the preferred embodiment of the present invention, the electrodes of sub-component 210 are formed by a gold layer on the CZT. Alternatively, platinum, carbon, or other conductive materials can be used. The detection elements 212 are formed by an array of electrodes on the lower surface of the sub-component 210. The spatial resolution of the gamma-ray detector 200 (FIG. 1) is determined in large part by the size of the detection elements 212. Performance and long-term stability are enhanced by passivating the areas of CZT crystal between the electrodes.

In an alternative environment, the array of detection elements 212 formed in the detection module 206 comprises separate CZT crystals, shown in FIG. 3A as four CZT crystals 218, 220, 222, and 224. The crystals shown are preferably 12.7 millimeters by 12.7 millimeters by 5 millimeters thick, comprising spectral grade CZT. Gold contact films or layers are affixed to top and bottom surfaces of each crystal 218–224. The electrodes on the bottom surface of each crystal form a pattern of gold squares, one square for each detection element. In the preferred embodiment, the gold squares are approximately 3 millimeters on a side. The lines of separation 216 between the squares are preferably passivated, thereby, producing greater than 100 megohms isolation between detection elements.

In the preferred embodiment, conductive epoxy is used to bond the electrodes of the detection elements 212 to the contact pads of the lower plate and the contacts of the lower plate to the input contact pads of the circuit carrier 214. Alternatively, other conductive bonding means may be used such as indium-bump bonding.

Thus, the detector inputs are connected to the ICs in the circuit carrier 214 via the surface of the carrier 214. Other inputs and outputs are connected to the ICs via a plurality of pins 240 on the bottom surface of the circuit carrier 214. The plurality of pins 240 are designed to mate with insertion or socket connectors affixed to the module board 208 (FIG. 2). As described above, prior art assemblies of semiconductor radiation detectors typically interface with conditioning electronic circuits in a manner that allows the assemblies to be butted on, at most, three sides. The configuration of the detection module 206 shown in FIG. 2 advantageously allows the detection module 206 to be butted on all four sides. Therefore, the present detection module 206 advantageously provides a modular element which can be combined in a number of ways with other detection modules 206 to produce a nuclear medicine imager having a desired configuration.

Figure 3B:
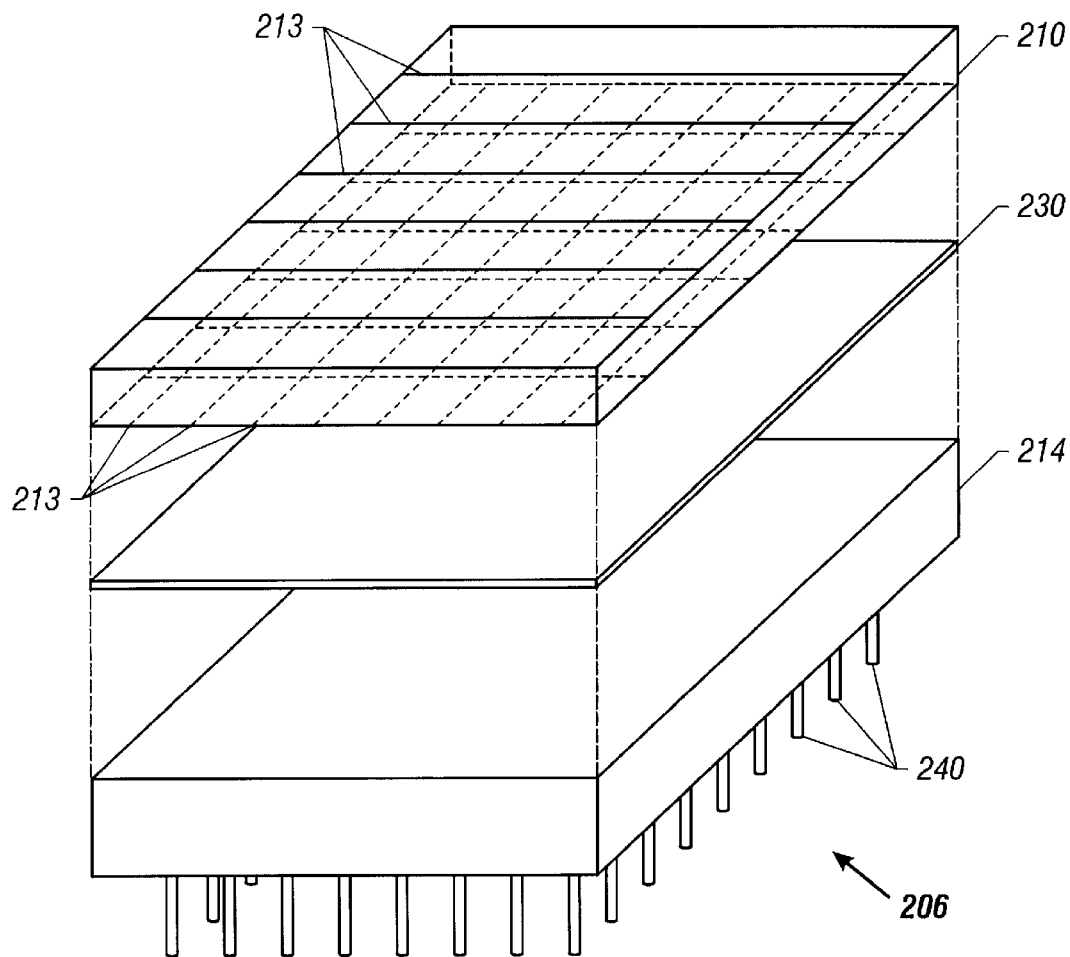
FIG. 3B shows an exploded perspective view of an alternative embodiment of the detection module shown in FIG. 2.
Figure 3C:
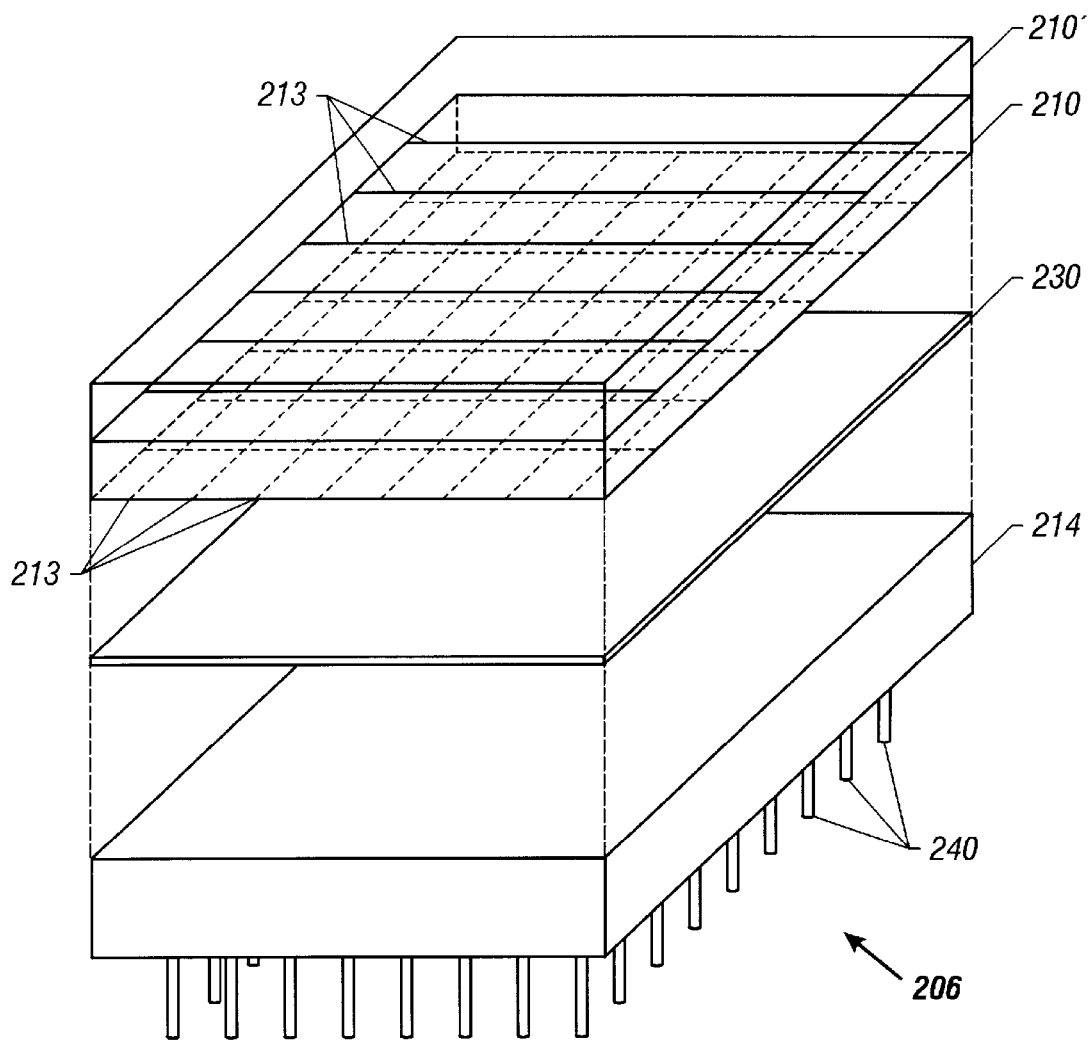
FIG. 3C shows an exploded perspective view of an alternative embodiment of the detection module shown in FIG. 2, this embodiment employing a downconversion element.

Alternatively, FIG. 3B depicts the same detection module 206 but with the array of semiconductor detection elements 213 formed by orthogonal strips on the upper and lower surfaces of sub-component 210. An advantage of using orthogonal strips is that the number of channels of signal conditioning is less for the same spatial resolution or the spatial resolution can be made finer with the same number of channels of signal conditioning. In this embodiment, the signals from the upper surface are connected to the inputs of the integrated circuits via a capacitor and resistor network. The alternative embodiment shown in FIG. 3B preferably has 32 upper strips and 32 lower strips on 1 mm centers in a module that has outer dimensions of approximately 32 mm by 34 mm. The module has a small dead space at only one edge and is constructed to minimize that dead space to allow the module to be fully buttable on 3 sides and buttable on 4 sides with a small dead space on only one side. The semiconductor material is made up of one or more elements with strips formed on the surfaces and interconnected as required to form the total array.

CZT crystals have been commercially available from Aurora Technologies Corporation of San Diego, Calif. since the late 1980's and from eV Products of Saxonburg, Pa. since 1993. Cadmium telluride is available from vendors in the U.S.A., Asia, and Europe.

In an alternative embodiment, indicated by FIG. 3C, the alumina or other insulating layer described above need not be employed. As stated above, the bare CZT crystal would then act as a broadband radiation detector. A crystal 210' of a downconversion material, such as CsI, or an array of such crystals, may be disposed adjacent the CZT layer, i.e., between the CZT layer and the incident radiation, to even further extend the radiation sensitivity. That is, a scintillation material such as CsI in combination with the CZT crystal allows the capture of gamma rays having energies from very low to very high. For example, a typical energy range detectable by this combination may be from about 1.2 eV to at least 1 MeV. CsI has certain advantages. First, it has a high enough atomic number so that it has good efficiency. Second, it has a high mechanical strength. Third, it is not deliquescent.

In this alternative embodiment, the electrodes of the subcomponent 210 may require modification. In particular, the electrodes may require patterning so that incident gamma rays, downconverted in the downconversion element, may impinge on the CZT. Without removal of some portions of the electrodes, the downconverted photons, which e.g. may be visible light, may not have enough energy to be transmitted through to the CZT.

Second Embodiment

The above embodiment describes a CZT-based or CsI/CZT-based detector. CZT-based detectors are based on the principle that incoming gamma rays are converted to electron-hole pairs which are then detected. The invention may also be implemented in detectors employing alternate materials. For example, CsI may be used as is described in the following embodiment. In this embodiment, an incoming gamma ray is downconverted to at least one lower frequency photon, these photons are then detectable by a photodetector array. Typically, an incoming gamma ray is downconverted to several photons of lower frequency or energy.

Figure 10:
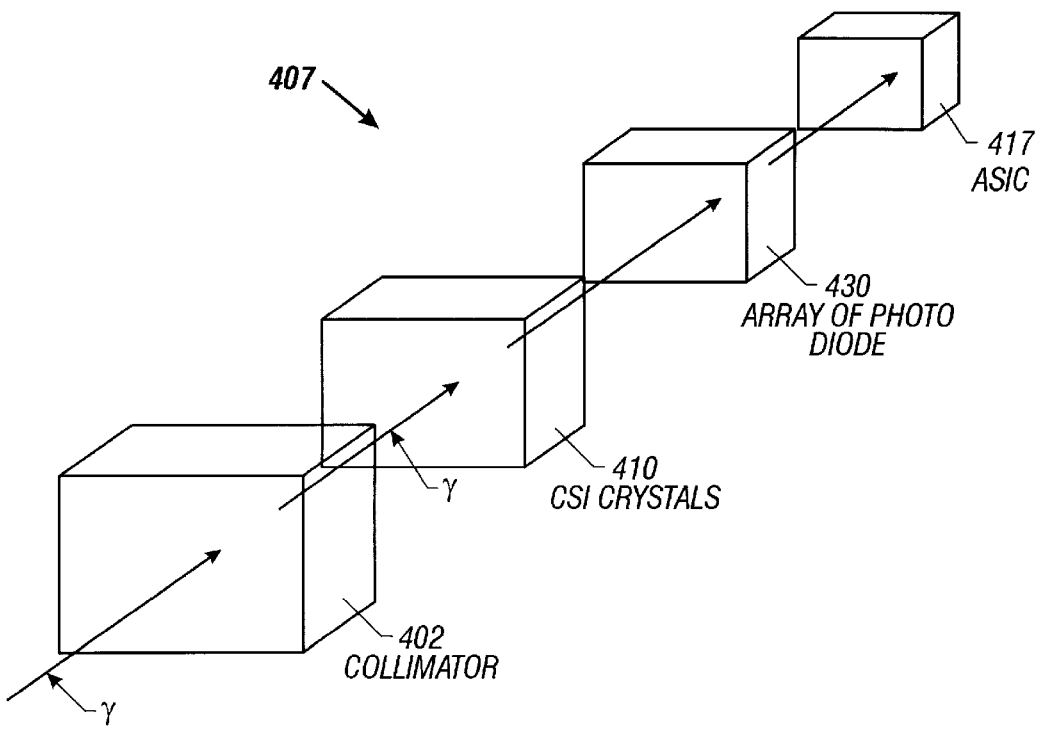
FIG. 10 is a perspective view of a preferred embodiment of a configuration of the detection module according to an embodiment of the invention using a CsI cell.

A module 407 is shown in FIG. 10 which is preferably capable of detecting energies in the range from a few keV to over several MeV. The major elements are as follows. A collimator 402 provides directional information. Downconversion cells 410 convert incident gamma rays to scintillation light or visible light photons. An array of photodetectors 430 detects the scintillation photons. A custom IC readout chip 417, such as an ASIC, then is used to read out the photodetector array information. Each of these elements is described in more detail below.

Collimator 402 is important for both spatial resolution and sensitivity in imaging devices. In the present invention, the collimator 402 may include a plurality of holes. The holes may be hexagonal, square, or other shapes. The use of square holes allows a 1-to-1 (or, e.g., 4-to-1) matching to square detector pixels. Further, such square hole matching eliminates artifacts due to geometric mismatch between hexagonal collimator holes and the square detector array. Additionally, the walls of the hole may be aligned with the edges of the detector elements. The shadow of the walls then falls on the inactive area of the detector elements.

Figure 11:
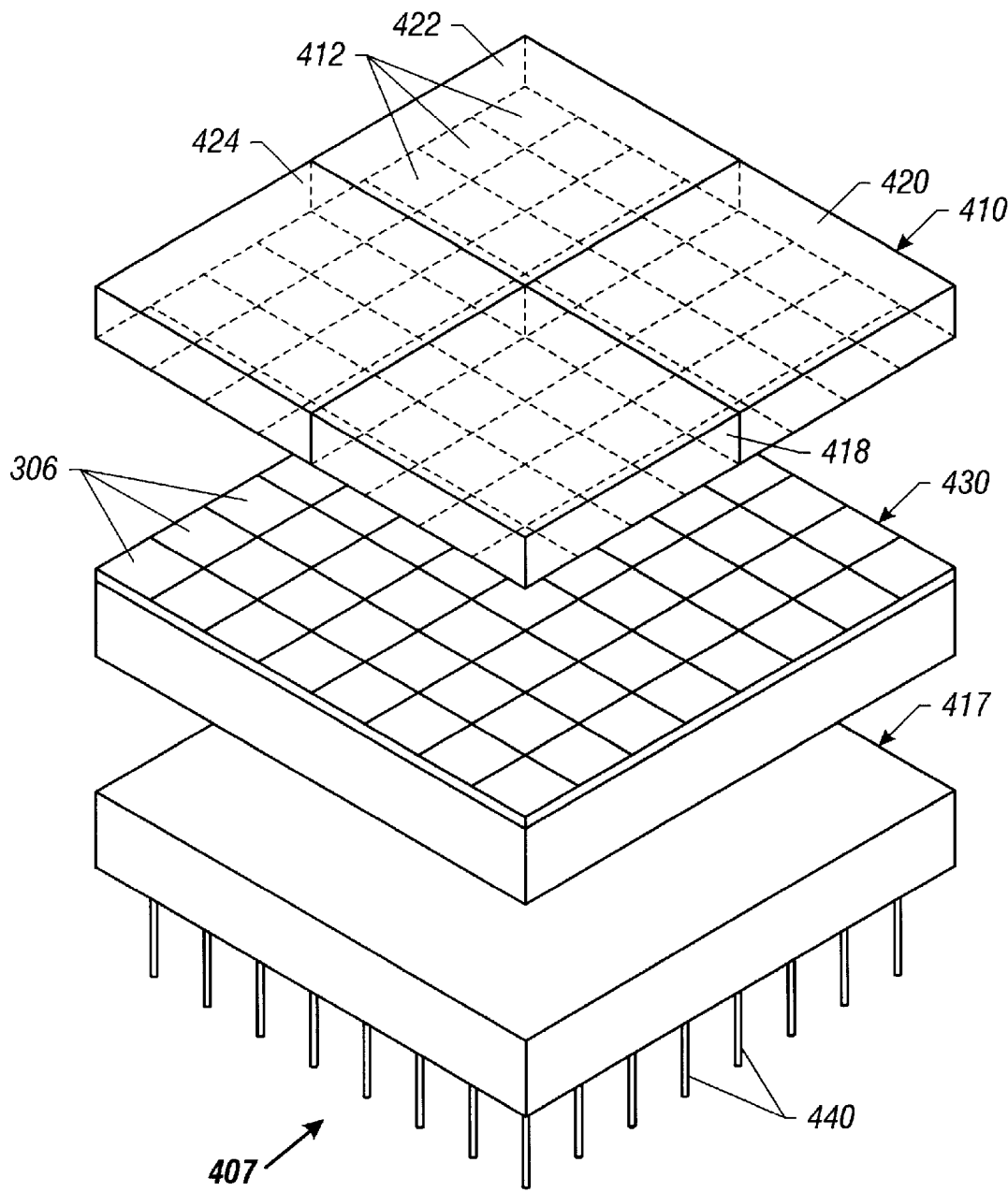
FIG. 11 shows an exploded perspective view of the detection module.

As further depicted in FIG. 11, the module 407 also includes an integrated circuit mounted within a package, such as a 1-inch square or rectangular ceramic, plastic, or glass epoxy carrier.

Sub-component 410 of the detection module 407 includes one or many downconverting cells 412. The cells 412 are preferably configured in an N×M array such as an 8×8 or 8×16 array. In the preferred embodiment of the present invention, the subcomponent 410 may comprise one or a plurality of downconverting crystals, such as cesium-iodide (CsI) crystals. The crystals can alternatively comprise other x-ray or gamma-ray sensitive materials.

Figure 12:
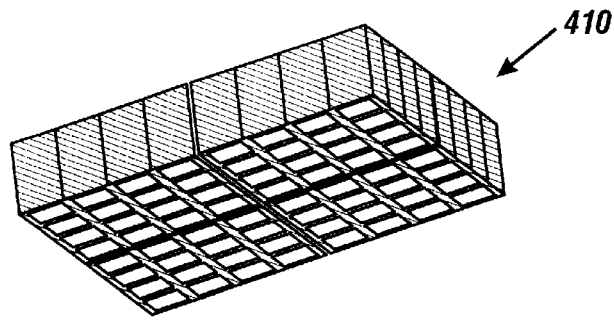
FIG. 12 is a perspective schematic view of a grouping of CsI cells, according to the principles of the present invention.

Referring also to FIG. 12, the array 410 of CsI cells 412 may be employed to shift or "down convert" the wavelength of impinging gamma rays to lower energy photons (e.g., those in the visible light spectrum) that are detectable by a photodetector array. In particular, an incoming gamma ray passing from collimator 402 into CsI crystal cell array 410 causes an ionization event which results in the formation of multiple photons emitted in the CsI crystal cell array 410.

Figure 13:
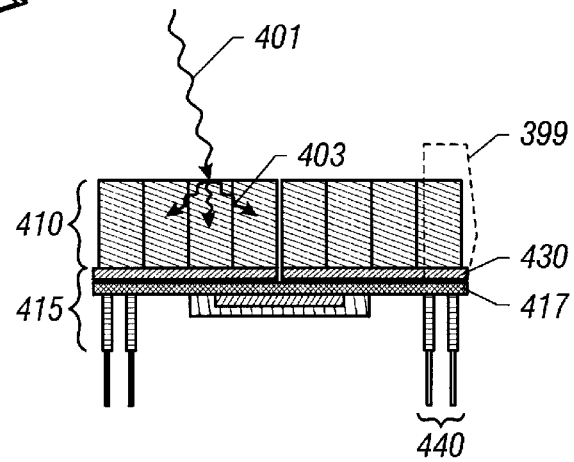
FIG. 13 is a side schematic view of a detector module according to the principles of the present invention.
Figure 14:
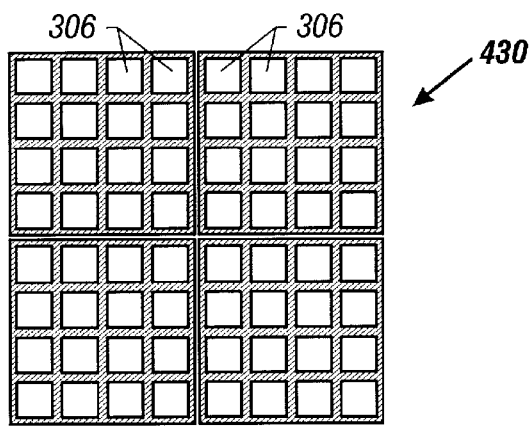
FIG. 14 is a top plan view of a set of photodetector array elements.

This situation is shown in FIG. 13. An incoming gamma ray 401 is incident in CsI crystal cell array 410. This event causes the emission of photons 403. These photons 403 are then incident on an array 430 of individual photodetector array elements 306, as shown in FIGS. 11 and 14. Photodetector elements 306 may advantageously employ, e.g., semiconductor detector elements. The combination of a CsI cell 412 and a corresponding photodetector element 306 is referred to here as a "detection element" 399 (FIG. 13).

The use of CsI has many advantages. CsI has a high density and effective atomic number. Therefore, this material shows a greater detection efficiency than many other types of scintillation crystals. Furthermore, CsI has one of the largest scintillation yields of any known inorganic scintillating crystal. Therefore, CsI offers high energy resolution and detection efficiency for gamma ray cameras. Mechanically, CsI is generally easier to work with and less fragile than semiconductors such as CZT. CsI is easy to machine into pixels. CsI crystals may be made thick. Thick CsI crystals may be easily implemented in a high efficiency detector. In an alternative embodiment, the CsI crystals may be activated by an activator such as thallium.

As noted above, photons 403 from the CsI array 410 are then incident on silicon photodetector array 430, which may be constructed from sub-arrays 411, each comprising a number of elements 306. Each element 306 may have one or a number of single photodetectors thereon. Such photodetectors may be designed for low dark current in order to minimize electronic noise. Such electronic noise is sometimes apparent at the long shaping times desirable for use with CsI crystals.

One type of photodetector includes a photon-sensitive layer of silicon, such as on a silicon wafer or chip. Another type of photo detector which may be used is a low noise solid state mercuric iodide ($HgI_2$) detector. Another example of construction of a photodetector array 430 which may be employed in the present invention is disclosed in "Fabrication of Detectors and Transistors on High Resistivity Silicon", by Steve Holland, *Nuclear Instruments and Methods in Physics Research*, Vol. A275, pp. 537–541 (1989). Other types of detectors which may be employed include the above-mentioned CZT detectors, silicon PIN diodes, avalanche photodiodes (APDs), gallium arsenide diodes, etc. Other appropriate and advantageous photodetectors include those having nonunity gains such as those employing avalanche photodiodes. Such photodiodes allow resolution to be achieved of even a single photon. Avalanche photodiodes, combined with scintillators, can achieve performance near that of solid-state detectors.

Other types of downconversion materials which may be advantageously employed include
Bismuth Germanate—BGO
Sodium Iodide, Thallium Doped—NaI(TI)
Yttrium Aluminum Garnate, Cerium Doped—YAG(Ce)
Yttrium Oxyorthosilicate, Cerium Doped—YSO
Yttrium Aluminum Perovskit, Cerium Doped—YAP
Lutetium Oxyorthosilicate, Cerium Doped—LSO
Lutetium Aluminum Garnate, Cerium Doped—LUAG
Lutetium Aluminum Perovskit, Cerium Doped—LUAP
Gadolinium Oxyorthosilicate, Cerium Doped—GSO
Cadmium Tungstate—CWO
Lead Tungstate—PWO
Barium Fluoride—BaF
Cesium Flouride—CsF
Calcium Flouride, Eruopium doped—CaF(Eu)
Zinc Sulfide, Silver doped—ZnS(Ag)

The detector of the invention is not limited to a single detector embodiment but rather can be used in a multi-detector configuration. In other words, a number of single detection elements 399 are generally grouped together to form an array of detectors, or, in accordance with the principles of the invention, a monolithic detector array can be fabricated. In fact, this embodiment has an advantage in that its modules are more easily made to be all-side buttable. In this embodiment, a conventional array of photodetectors may be employed.

Figure 15:
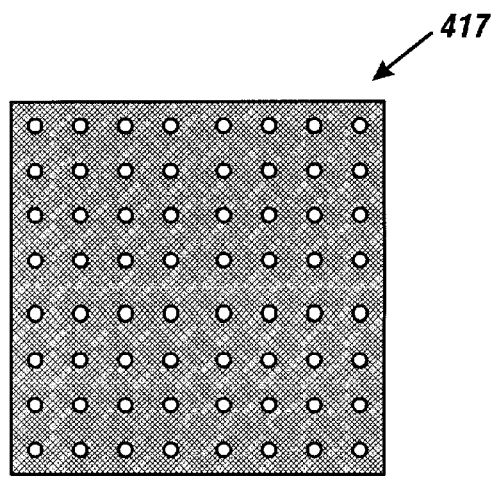
FIG. 15 is a top plan view of multichip module electronics.

The results of the measurements of the photodetectors 306 may be monitored and read out by a custom IC or ASIC 417, as shown in FIGS. 10, 11, and 15. Considerations for the design of the ASIC may include the signal properties of CsI or any other such properties which affects data handling and management. Each ASIC 417 may be part of a multichip module ("MCM") whose cumulative data may be patched together in a computer to form a complete image of the object. The ASIC 417 may be part of a housing unit 415 (see FIG. 13) which houses the ICs and passive components, and provides interconnections from the ICs to the photodetectors 306 and to the module board 300. The housing unit preferably comprises ceramic, plastic, or various glass epoxies.

Previous detection modules like those shown in FIG. 11 were assembled with thin plates positioned on both the top and bottom surfaces of the sub-component crystal. The upper plate provided a means for applying a bias voltage to the detection modules, insulated the bias voltage from the detector housing, and provided physical protection for the crystals. The present invention has the advantage that such plates are unnecessary. The output from a CsI crystal is a photon, not an electron, and thus no bias voltage is required.

The array 410 of cells 412 fonned in the detection module 407 may comprise one or more separate CsI crystals, shown in FIG. 11 as four CsI crystals 418, 420, 422, and 424. The crystals shown may be from a few millimeters to several centimeters thick (e.g., 2½ centimeters thick). The crystals may even be thinner, e.g., less than half-a-millimeter thick, if the application allows.

The photodetector 306 inputs are connected to the ASIC 417 in the housing unit 415 (see FIG. 13). Other inputs and outputs are connected to the ICs via a plurality of pins 440 on the housing unit 415. The plurality of pins 440 are designed to mate with insertion or socket connectors affixed to the module board 208 (FIG. 2). As described above, prior art assemblies of semiconductor radiation detectors typically interface with conditioning electronic circuits in a manner that allows the assemblies to be butted on, at most, three sides. The configuration of the detection module 407 shown in FIG. 1 advantageously allows the detection module 407 to be butted on all four sides. One reason for this, as mentioned above, is that photodetector arrays are known which may be buttable on all four sides. Therefore, the present detection module 407 advantageously provides a modular element which can be combined in a number of ways with other detection modules 407 to produce a nuclear medicine imager having a desired configuration and a desired size.

It is also noted that while the detection module 407 may be butted on all four sides, it is not necessary that the photodetectors 306 be fully buttable on all four sides. In many cases, the photodetectors 306 may be slightly smaller than the area of a CsI cell (element 412 in FIG. 11). The CsI cell may be coated with a reflective material which may be used as a convenient way to isolate crystal cells 412. Photons which are not initially directed at a photodetector active element may reflect off the reflective material into the photodetector active element, retaining efficiency. The edges of the areas which are coated with the reflective coating are then unable to downconvert photons. These edges, termed here "dead areas", are conveniently aligned with corresponding septal walls of the collimator 402. These areas need not be considered completely unable to downconvert photons; however, their sensitivity is very considerably less than the areas of downconversion material which are not adjacent a deflective coating. Thus, they are considered effectively "dead." In this way, the holes of the collimator 402 are aligned with the active areas of the CsI cells. Correspondingly, the reflective areas may be conveniently aligned with the non-active areas between photodetectors 306.

As mentioned above, the modules may be all-side buttable. For example, the modules may be square and form an N×M array, such as an 8×8 array. The N×M array may be of a size and shape suitable to image an organ of the human body. The array may be circular, linear, or even nonplanar as the application dictates.

The following description of the detector electronics is primarily for the first embodiment (employing CZT). However, the electronics for a detector employing a CsI crystal is analogous.

Detection Module Board

Figure 4:
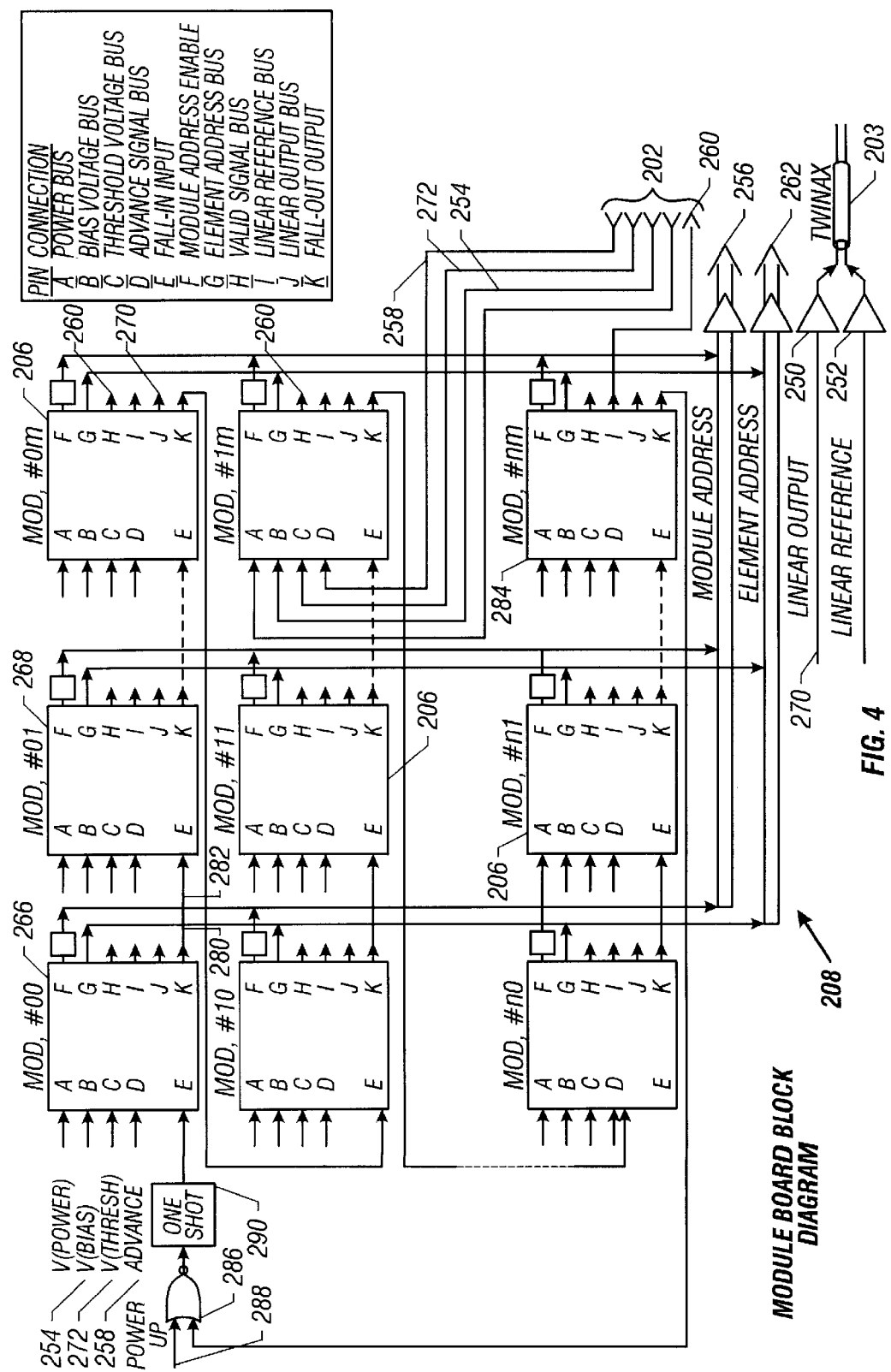
FIG. 4 shows a block diagram of the electronics board of the detection module board shown in FIG. 2.

FIG. 4 shows a block diagram of the detection module board 208 shown in FIG. 2. The detection module board contains an array of socket connectors into which each detection module 206 shown in FIG. 2 is inserted. Alternatively, the modules can be soldered into the module board. FIG. 4 shows the interconnection of the detection module input/output pins. In one embodiment, the gamma-ray detector 200 comprises 35 detection modules arranged in a 5×7 array. However, the array size used in the illustrated embodiment is exemplary only, and should not be taken as a limitation of the present invention. The gamma-ray detector 200 of the present invention may comprise X detection modules 206, arranged as an N×M array or as any shape or size. The only difference between such an N×M array camera and the illustrated embodiment example is the way the modules are mapped in the image and the number of address lines required. For example, in one embodiment, six address lines specify the location of sixty-four detection modules 206 arranged in a square pattern. The same sixty-four elements could also be arranged in any other desired shape, such as rectangular, circular, as an annular ring or a cross. In an embodiment having a 16×16 array of detection modules, eight active lines are required on the module address bus 256.

Each detection module 206 shown in FIG. 4 is mated to a corresponding socket connector (not shown) soldered or otherwise affixed and electrically coupled to the module board 208. The sockets are closely packed together on the module board 208 with the detection modules 206 butted against each other on all four sides when the modules are fully engaged and mated with the sockets. The module board preferably includes "push holes" (not shown) at each module location which allow a technician to install or remove the modules 206 from the sockets without damage during testing and servicing.

Both digital and analog signals are routed in a known fashion to each socket via traces in the module board 208 as schematically shown in FIG. 4. The digital signals and supply lines are provided to the module board 208 via input and output ports that are connected to the digital communications link 202 (FIG. 2). As shown in FIG. 2 and described below in more detail with reference to FIG. 8, the digital communications link 202 is connected to the signal processor 300. The analog signals, output by each detection module 206, are bussed together on the module board 208 and routed via linear buffers 250, 252 to the signal processor 300 (FIG. 2) via an analog link 203, preferably a twin-axial cable. The cross-talk between the analog and digital signals is thereby greatly reduced by conditioning and shielding the analog output signals and by transmitting the analog and digital signals over separate communication links 202, 203.

In the embodiment shown in FIG. 4, the detection modules have a plurality of input/output pins 240 (FIG. 3A and FIG. 11) which mate with corresponding insertion connectors in the module sockets affixed to the module board 208. The pin-function list for each module socket of the illustrated embodiment is given below in Table 1. Pins and functions listed below have corresponding integrated circuit input/output functionality as is described below with reference to FIG. 4.

Ground connections, bias signals, and supply voltages are routed to the detection modules 206 via internal layers of the detection module board 208. Power pins are connected to bypass capacitors (not shown) which bypass the power supplies to respective ground planes. Digital and linear signals are buffered on both the module board 208 and on the signal processor 300 (FIG. 2). Table 2 shows the pin function list for the digital communications link 202 which couples the module board 208 with the signal processor 300.

TABLE 1

Detection Module Pinout Function List

| PIN | FUNCTION | INPUT/OUTPUT |
|---|---|---|
| 1–6 | Element Address | Output |
| 7 | Fall In | Input |
| 8 | Fall Out | Output |
| 9 | Valid | Output |
| 10 | Address Enable | Output |
| 11 | Advance | Input |
| 12 | Linear Reference | Output |
| 13 | Linear Output | Output |
| 14 | Threshold | Input |
| 15 | Threshold Reference | Input |
| 16 | Analog Power #1 | n/a |
| 17 | Analog Ground #1 | n/a |
| 18 | Analog Power #2 | n/a |
| 19 | Analog Ground #2 | n/a |
| 20 | Digital Power #2 | n/a |
| 21 | Digital Ground #2 | n/a |
| 22 | Test Signal (Linear) | Input |
| 23 | Test Shift Register CLK | Input |
| 24 | Test Shift Register Data In | Input |
| 25 | Test Shift Register Data Out | Output |

TABLE 2

Wire List for Link 202

| WIRE | FUNCTION | INPUT/OUTPUT |
|---|---|---|
| 1–6 | Element Address | Output |
| 7–14 | Module Address | Output |
| 15 | Valid | Output |
| 16 | Advance | Input |
| 17 | Threshold | Input |
| 18 | Bias Voltage | n/a |
| 19 | Analog Power | n/a |
| 20 | Analog Ground | n/a |
| 21 | Digital Power | n/a |
| 22 | Digital Ground | n/a |
| 23 | Buffer Power | n/a |
| 24 | Buffer Power | n/a |
| 25 | Buffer Ground | n/a |
| 26 | Chassis Ground | n/a |
| 27 | Test Signal | input |
| 28 | Test Data | input |
| 29 | Shift Register #1 | input |
| 30 | Shift Register #2 | input |

In the preferred embodiment, the signals provided from the signal processor 300 to the detection module board 208 include voltage and ground references and the "advance" signal. As described below in more detail, the address and "valid" signals and the analog outputs are provided from the detection module board 208 to the signal processor 300 when a fall-through addressing identifies a valid event in a detection element 212. These signals are bussed to every detection module 206 on the module board 208. For example, all of the valid lines of the detection modules 206 are bussed together on line 260. The bias voltage (preferably 200–500 volts) is connected to the top surface of each detection module and excites the detection elements 212 during camera operation.

Both module and element addresses are supplied to the signal processor 300 via common address lines 256, 262 connected from each detection module location on the module board 208. The module address bus 256 and the element address bus 262 are logically combined to create an n-bit wide address bus. In the preferred embodiment, the address bus transmitted to the signal processor 300 is 14-bits wide. In the preferred embodiment, the module address lines 256 are treated by the signal processor 300 as the most-significant-address bits, and the element address lines 262 are treated as the least-significant-address bits. The address busses 256, 262 are driven by tri-state buffers at each detection module location. Only one detection module 206 asserts an address on the address busses 256, 262 at a given time.

In the preferred embodiment, the module address of each detection module 206 is "hard-wired" into a tri-state transceiver located at each module on the module board 208. That is, the binary address for each module socket is pre-wired by connecting the appropriate bits to digital ground and power. As described below in more detail with reference to FIGS. 5–7, when the fall-through addressing arrives at a detection module with valid data, that module outputs an analog signal (via a linear signal out line 270), a "valid" signal, an "address enable" signal, and the address which uniquely identifies the detection element 212. The digital IC in the detection module 206 asserts the detection element address on the address bus 256, and a tri-state address buffer at that module location asserts the detection module address on the bus 262 when an "address enable" signal is asserted true. The detection modules 206 are therefore designed to be completely interchangeable. The detection modules 206 therefore are not "addressed" by the data acquisition computer 400 in a conventional sense. Rather, as described below in more detail with reference to FIGS. 5–7, the modules 206 initiate the address when an event occurs. As shown in FIG. 4, the detection modules 206 are linked together in a "daisy-chain" configuration by coupling the "fall-out" output signal from one module (e.g., fall-out signal 280) to the "fall-in" input signal of a successive module (e.g., fall-in signal 282). As described below, the "fall-in" and "fall-out" signals are used to implement the "fall-through" data scheme of the present invention.

As described below in more detail, when a detection module 206 asserts a valid signal on line 260, the signal processor 300 reads and processes that detection element's address on the "address" lines and analog signal on the "linear output" line. The signal processor 300 then re-initiates the fall-through addressing and data acquisition process by generating and sending an "advance" signal over the digital communications link 202.

Detection Modules—Interconnection of the Analog and Digital Integrated Circuits

The circuit carrier 214 preferably contains three integrated circuits: two identical analog application specific integrated circuits (ASICs) and one digital ASIC. The two analog ASICs amplify and shape the analog signals for processing by the digital ASIC. The digital ASIC compares the analog signals generated by the analog ASICs with a reference or threshold voltage. If the signal is greater than the threshold (a "valid hit"), a latch is set which causes the analog value to be stored in a peak detection circuit. When enabled by a fall-through signal, the digital ASIC generates a "valid" signal and an "address enable" signal. Interconnections within the detection module 206 between the two analog ASICs 700 and a digital ASIC 800 are shown in the block diagram of FIG. 5A. The 64 signals from the detection elements 212 are connected to the inputs of the analog ASICs via thick-film capacitors in carrier 214. The leakage current from each detection element 212 is routed to ground via thick-film resistors also lithographed on the carrier 214.

Although the present invention is shown having two analog ASICs 700 in each detection module 206, one skilled in the art will appreciate that the signal conditioning functions performed by the analog ASICs 700 can be implemented in an alternative embodiment within one ASIC 700 and that the number of analog channels in one ASIC 700 could be either greater or less than 32. Further, the present invention contemplates combining the analog and digital processing functions on a single integrated circuit.

Because the detection elements 212 produce low amplitude electrical pulses when irradiated, any noise created during the processing of these signals can adversely affect the resultant image. The present invention significantly reduces crosstalk and noise by separating the analog and digital circuitry into separate ASICs.

Figure 5A:
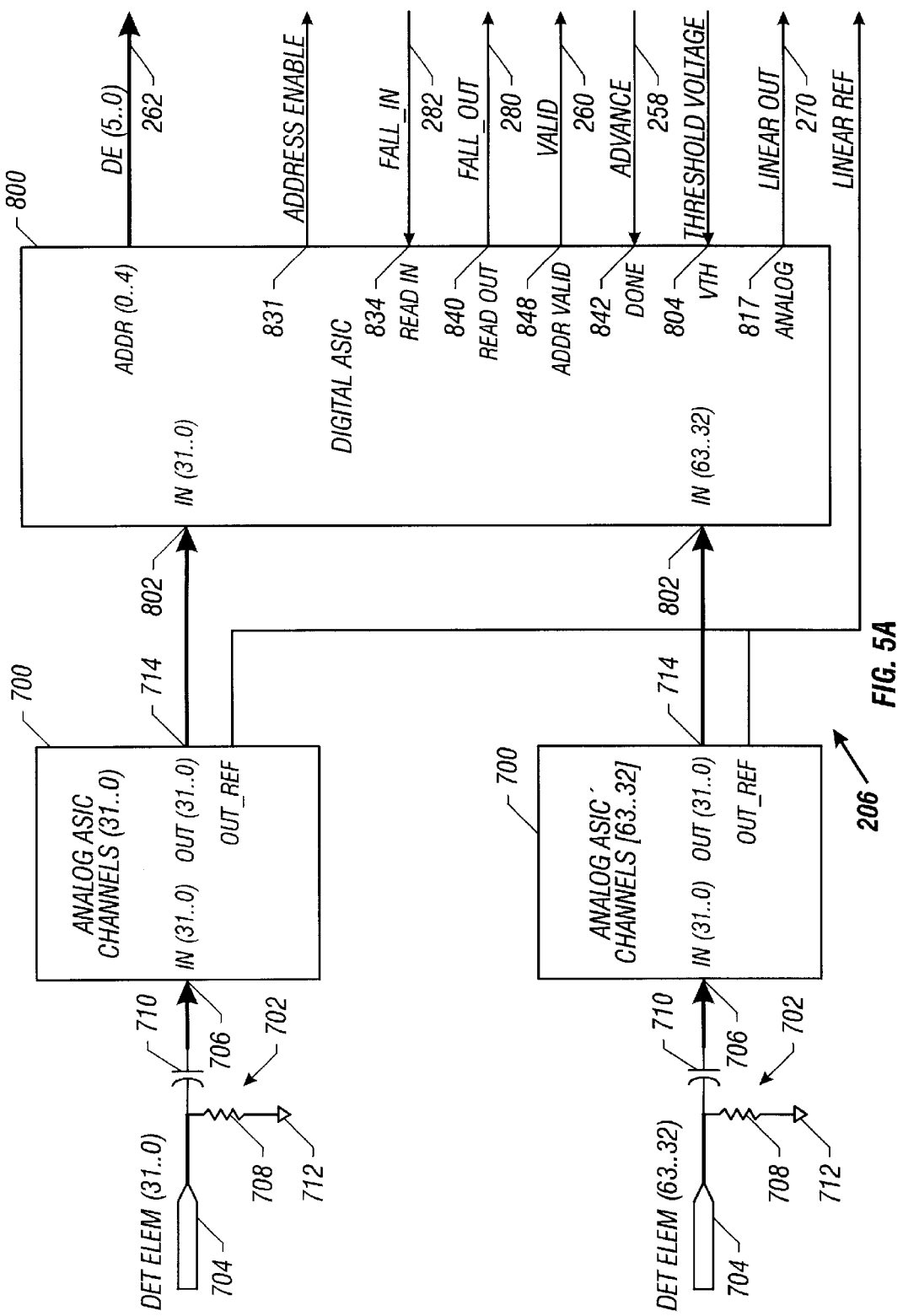
FIG. 5A is a block diagram of the electronics board of the detection modules shown in FIG. 4 showing the interconnection of signals between analog and digital ASICs used to implement the detection module functions.

Some prior art imaging devices use ASICs that require that the preamplifier associated with each detection element 212 be reset periodically to compensate for detector and amplifier input currents. This resetting is typically accomplished with an analog switch connected across the preamplifier feedback path. The operation of the switch causes large, spurious signals and momentarily incapacitates the amplifier. Passive feedback networks are difficult to implement because high resistance values must be used to effectively reduce the noise levels. The production of such high-value resistors is not currently possible. As shown in FIG. 5A, the present invention eliminates the detector current portion of this problem by placing a resistor/capacitor network 702 between an input port 704 and its associated input pad 706 on each input of the analog ASIC 700. The resistor/capacitor network 702 shunts leakage current from the detection element 212 to an analog ground 712 on the module board 208 before the leakage current enters the analog ASIC 700. Typical values for the resistor 708 and the capacitor 710 of the resistor/capacitor network 702 are 200MΩ and 100 pF, respectively. The amplifier input current is compensated by using a high output impedance amplifier as the feedback element around the preamplifier. Each detection element 212 of the 8×8 array of each detection module 206 is electrically coupled to an input port 704 on the circuit carrier 214. The signals generated by the detection elements 212 and transmitted to the 64 input ports 704 are relatively low-level signals ranging in values from 6000 to 60,000 electrons.

Assertion of the valid line 260 by one of the detection modules 206 indicates that at least one of its detection elements 212 has received a hit that requires processing and that it was selected by the fall-through addressing. Following a valid hit and after waiting a short time period which is sufficient to allow the linear signal to stabilize within the peak detector, the digital ASIC 800 enables an internal gate and waits to be enabled by a fall-through signal which is described below in more detail. Valid hits can be concurrently stored for all detection elements 212 in the detection module 206 by the digital ASIC. After a detection element 212 receives a valid hit, it waits to be enabled by a fall-through signal. The ASIC 800 then asserts a "valid" signal on output line 260 and an address enable signal on output pad 831. As described above and shown in FIG. 4, the valid lines 260 of all of the detection modules 206 are electrically coupled together and the valid signal is transmitted to the signal processor 300 over the digital communications link 202.

Thus, if any of the detection elements in the gamma-ray detector 200 produce a valid hit, the valid and address enable signals are asserted for that detection element when it is enabled by the fall-through signal. A peak detector in each channel of the digital ASIC 800 stores the amplitude of the charge pulse received from the detection element 212 until it is read by the signal processor 300. As shown in FIG. 5A, the stored analog signal is provided to the signal processor 300 through an analog pad 817 which is coupled with the linear bus 270. The hit is held within the digital ASIC 800 until it is read, processed, and cleared by an advance signal 258 produced by the signal processor 300. Each peak detector within the digital ASIC 800 stores the amplitude of the highest amplitude of successive hits generated by a detection element 212 until it is reset by the signal processor 300. The "hold droop" of the peak detector is preferably approximately no greater than 0.0001% per microsecond.

When the signal processor 300 completes processing the event, it asserts an "advance" signal on advance signal line 258. As shown in FIG. 4, the advance signal line 258 of each module 206 is electrically coupled together. When the advance line 258 is asserted true, the active detection module 206 (i.e., the detection module which presently has control of the address busses 256, 262 and the linear bus 270) clears the active output lines (valid line, address lines, and linear signals) and allows the fall-through signal to advance to the next latched detection element.

Fall-through Circuit

Figure 5B:
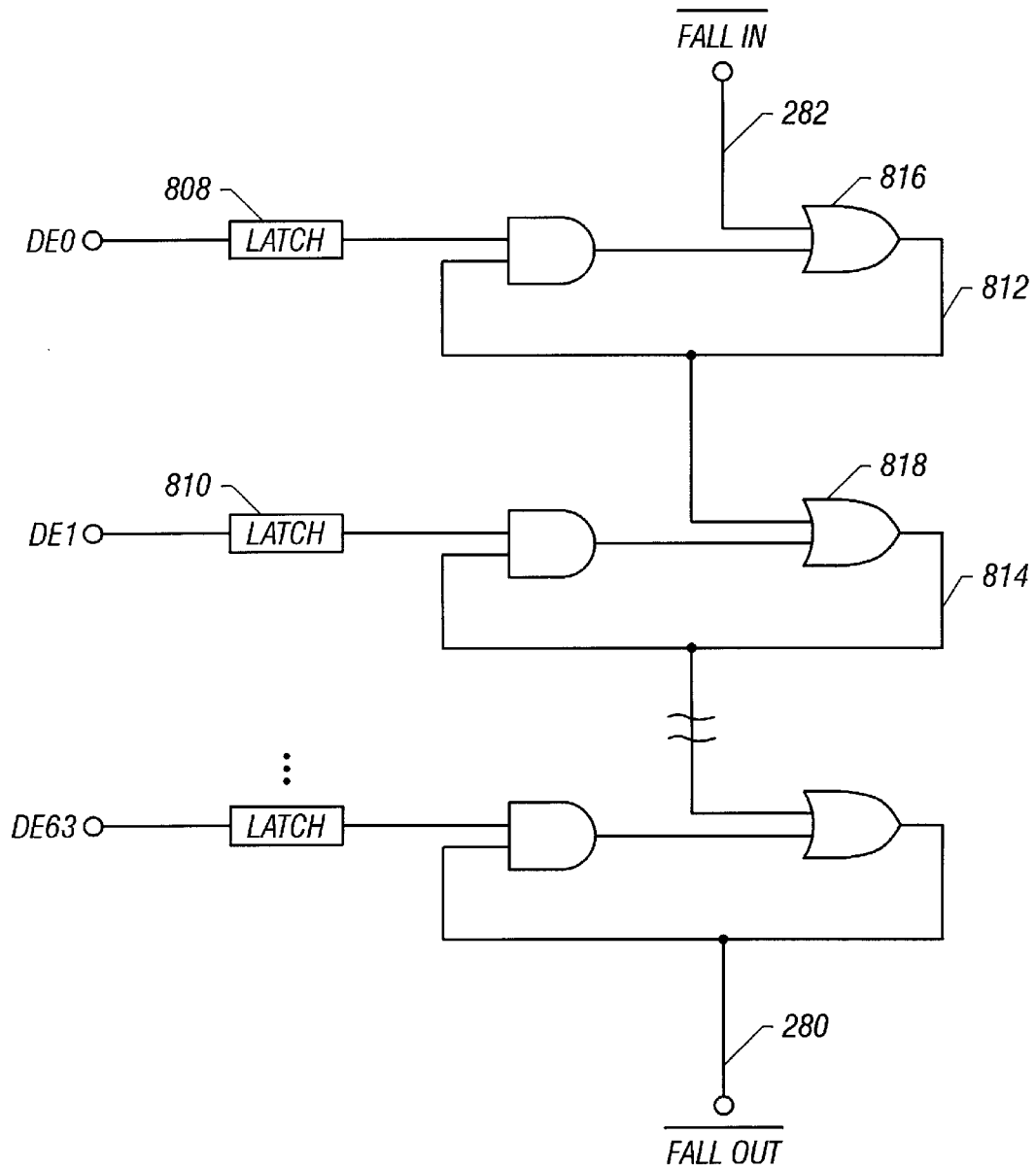
FIG. 5B is a simplified block diagram of a fall-through circuit used to read valid events recorded in the detection element conditioning and processing channels of the present invention.

A fall-through circuit is included in ASIC 800 for each detection element. A simplified block diagram of the fall-through circuit is shown in FIG. 5B as a series of logical "AND" and "OR" gates coupled together. This depiction of the fall-through circuit is given simply to describe its function. Each detection element 212 has a corresponding latch within the ASIC 800 for storing valid hits received by the detection element 212. For example, as shown in FIG. 5B, latch 808 stores a hit received by the first detection element (DE 0), latch 810 stores a hit received by the second detection element in the 8×8 array (DE 1), and so on. The latch outputs are coupled to corresponding fall-through blocks 812, 814. Block 812 has a first input of its OR gate 816 coupled to the fall-in signal line 282. The fall-in and fall-out signal lines of the detection modules 266 on the board 208 are "daisy-chained" together (FIG. 4). For example, the fall-out signal line 280 of detection module 266 is coupled to the fall-in input 282 of the next detection module 268. The last detection module 284 of the array of detection modules 206 has its fall-out line 280 coupled to a NOR gate 286. The output of the NOR gate 286 is coupled to the fall-in input 282 of the first detection module 266.

Therefore, the fall-through circuits within each detection module 206 of the gamma-ray detector 200 are all tied together, forming one circular fall-through loop. The NOR gate 286 allows the fall-through system to be initialized during a power-up sequence. For example, at power up, a PWR_UP signal 288 is asserted high which causes a one-shot multivibrator 290 to de-assert a logical 0 pulse on the fall-in signal line 282 of the first detection module 266. Referring again to FIG. 5B, if the first detection element latch 808 of the first detection module 266 is not set (i.e., the first detection element 212 associated with the latch 808 has not received a valid hit), the OR gate 816 will output a logical low value. The logical low is input into an OR gate 818 of the next fall-through block 814 which is associated with the next detection element 212 of the 8×8 array of detection elements 212 (e.g., "DE 1"). If the next detection element latch 810 is not set (i.e., the second detection element 212 associated with the latch 810 has not received a valid hit), the OR gate 818 will also output a logical low value. The subsequent fall-through blocks will similarly continue to produce a logical low value which progresses through the chain of fall-through blocks until a detection element is found which has received a hit and has thereby set its corresponding latch. If no detection element 212 within a detection module 266 received a valid hit, that is, if the digital ASIC 800 of detection module 266 does not have a latch set, the detection module outputs a logical low from its fall-out signal line 280. The low value is input to the fall-in input line 282 of the next module 268. Thus, the logical low progresses through the OR gates of each succeeding module until an element that has an event ready for processing is encountered or the signal passes out of the last module and back into the first.

A logical high input to any OR gate (i.e., OR gates 816, 818, and so on) stops the fall-through process. When an event is found, the digital ASIC 800 activates tri-state buffers (not shown) which allows the ASIC to take control of both the digital address busses 256, 262 and the linear signal line 270 (FIG. 4). The address of the detection element 212 which received the hit and which subsequently caused the fall-through circuit to halt is output onto the element address bus lines 262 by the ASIC 800. The address of the ASIC's detection module 206 is also asserted from the transceiver onto the module address lines 256 by the address enable line 832. As described above, the module address is hard-wired on the module board 208 into an 8-bit transceiver that is enabled by the address enable signal. The analog signal of the detection element 212 which caused the fall-through process to halt is selected using the detection element address output 262 of the digital ASIC 800.

The valid signal resulting from a hit causes the signal processor 300 to read and process the address and the analog signal. No other detection module can access the bus lines because the fall-through configuration ensures that only one detection module 206 is enabled at a time. The fall-through process remains halted until the signal processor 300 completes processing the event and asserts an "advance" signal over the advance signal line 258 which is shared by every detection module. When the active detection module receives the advance signal, it performs the following functions in sequence: resets the peak detector which is currently addressed; it de-asserts the valid signal causing the valid signal line 260 to assume a logical low value; it de-asserts the address enable signal; it disables its tri-state buffers, thereby, releasing the address and signal busses; and it asserts a logical low pulse over its fall-out line. The fall-through process resumes with the next fall-through block in the digital ASIC 800.

Because the fall-through scheme scans detection elements in a sequential manner, one element at a time, detection elements 212 that receive a valid hit cannot affect or interrupt the scanning of other detection elements. All elements are "latched-out" or inhibited until they are read during a subsequent fall-through scan. Thus, each detection element 212 of each module 206 is given an equal opportunity to be serviced by the signal processor 300.

Integrated Circuits (ICs)

Figure 6:
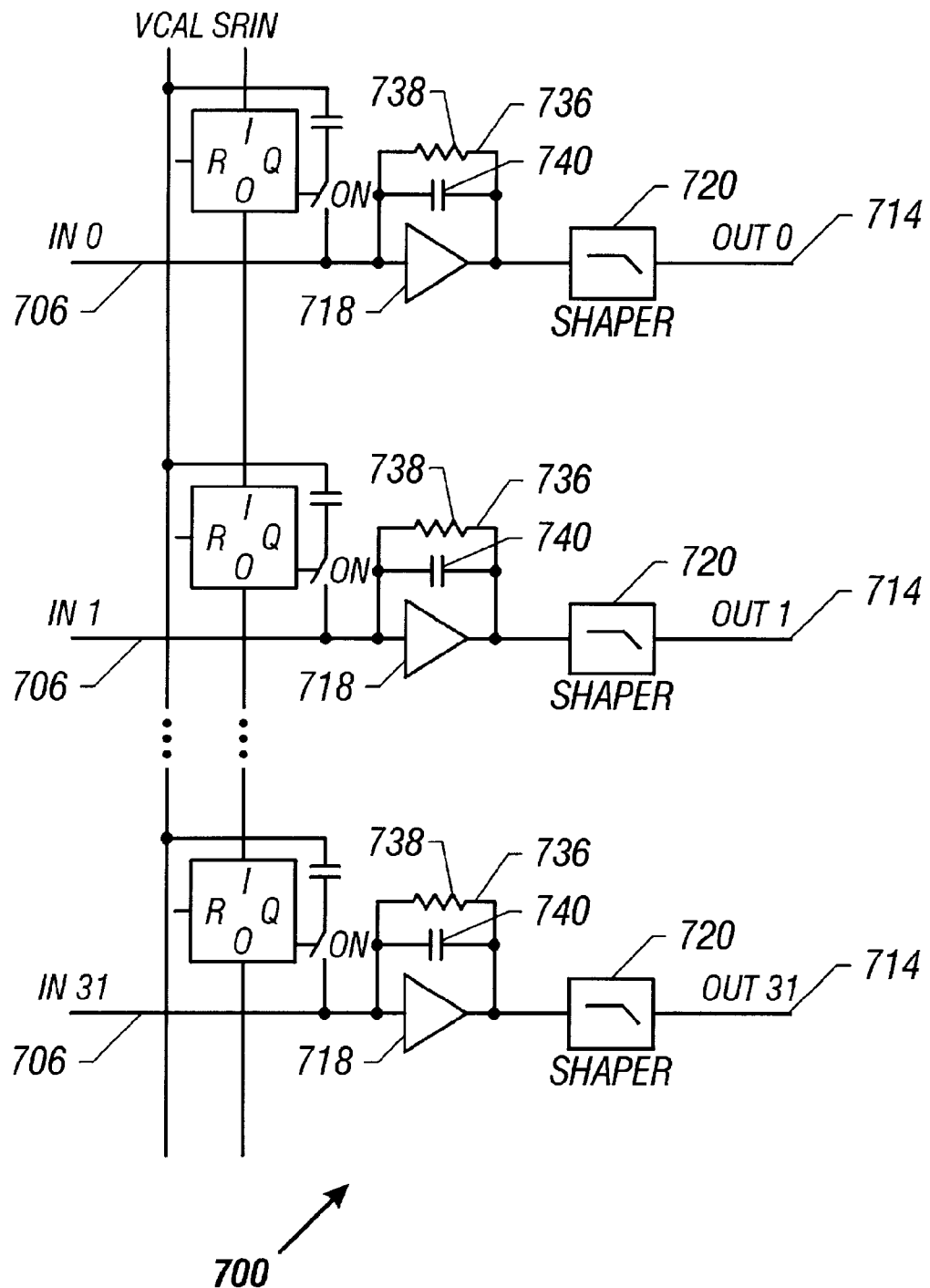
FIG. 6 is a block diagram of the analog ASIC shown in FIG. 5A.

FIG. 6 shows a block diagram of the analog ASIC 700 of FIG. 5A. Preferably, each analog ASIC 700 includes thirty-two channels. Each channel preferably has an input pad 706 for receiving and conditioning the analog signal produced by its associated detection element 212 when a gamma-ray is absorbed. Each channel includes a charge amplifier 718 and a shaping amplifier 720. The preamplifier incorporates a current-sourcing amplifier (indicated by resistor 738 in FIG. 6) to maintain the DC stability of the circuit. The rise and fall times of the shaping amplifier are set via resistors external to the ASIC 700.

The preferred value of the capacitor 740 is selected to provide a desired delay time. The amplifiers 718 are designed to amplify the pulses generated by the detection elements 212 to levels which can trigger comparators within the digital ASIC 800. Preferably, the amplifiers 718 amplify the analog signals to levels approximately equal to one volt.

The peaking and fall times of the shaping amplifier 720 is chosen to minimize white and 1/F noise contributions and to obtain good baseline recovery. Preferably the peaking time is 0.1 to 1.0 microsecond with fall times of 1 to 10 microseconds. The outputs of the shaping amplifiers 720 are coupled to the inputs of corresponding peak detectors in the digital ASIC 800.

Figure 7:
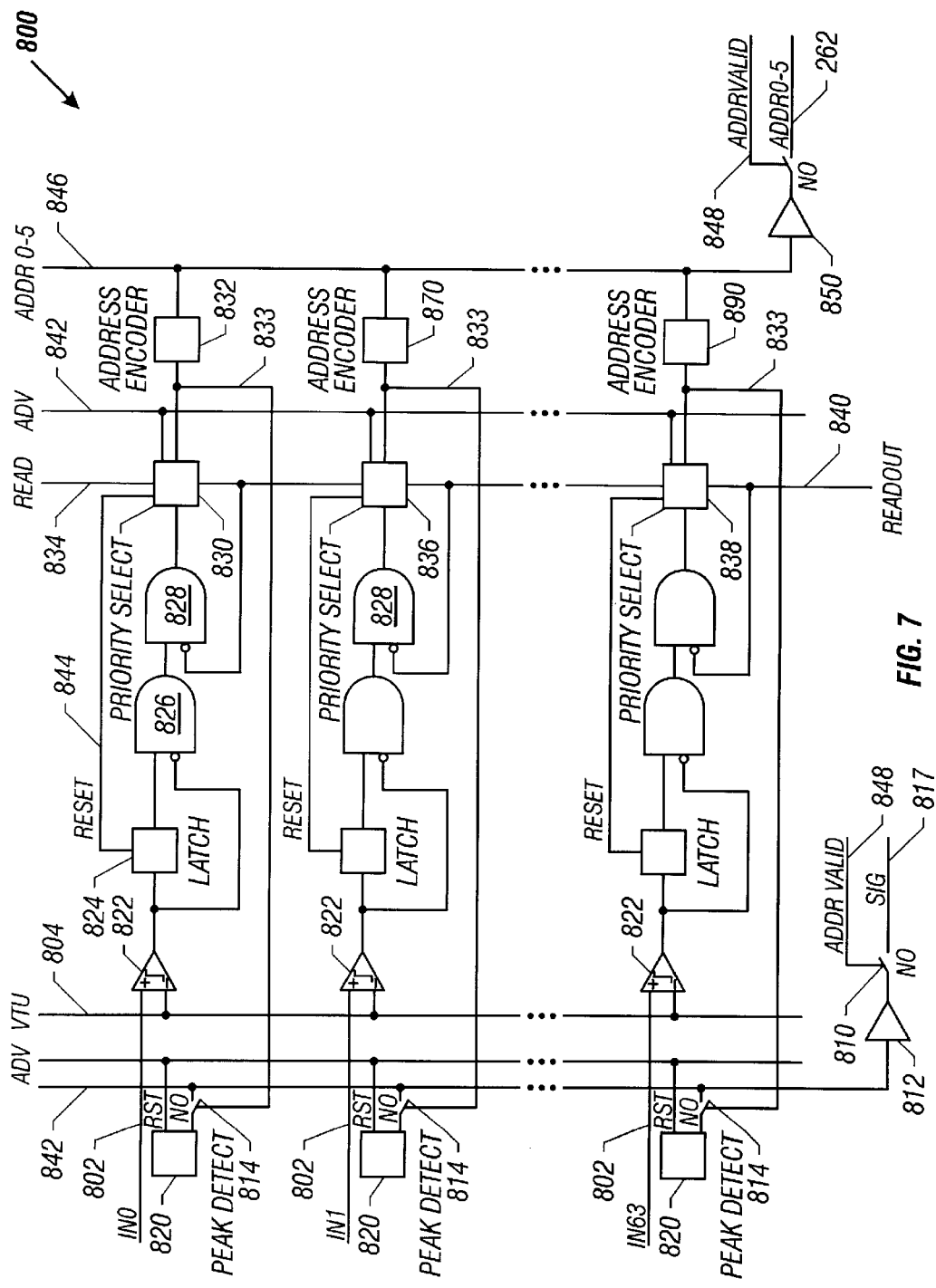
FIG. 7 shows a block diagram of the digital ASIC shown in FIG. 5A.

As shown in FIG. 7, the digital ASIC 800 preferably includes sixty-four parallel channels corresponding to the sixty-four detection elements 212 associated with each detection module 206. Each channel includes a peak detector 820, a comparator 822, an event latch 824, AND gates 826, 828, a fall-through block 830, and an address encoder 832.

As described above with reference to FIG. 5A, the peak detectors 820 perform an analog peak detection function by storing the highest of successive pulses generated by the detection elements 212 until a valid signal "locks out" any subsequently generated pulses. The subsequently generated pulses are "locked out" until the peak value is read. The switch 814 allows the analog signal from the selected peak detector to be transmitted to the signal processor 300 via the linear out_sig line 817 when that detection element address is valid.

As shown in FIG. 7, the peak detectors 820 include control lines 833 coupled from the fall-through blocks (830,836, 838) to the switches 814. The switches 814 couple the output of a selected peak detector 820 to the signal buffer 812 when actuated by a control line 833. The analog voltage stored by any one peak detector 820 is reset by the advance signal 842 if and only if the address of that element is enabled. That is, when a switch 814 is activated by a fall-through block (e.g., 830), the peak detector connected to the activated switch 814 is reset when the advance signal 842 is asserted. Thus, after the signal processor 300 processes an event stored by a peak detector, it clears the selected peak detector 820 to allow it to begin accumulating subsequent hits.

The buffer/driver 812 is coupled to switch 810. The switch 810 is controlled by an address valid signal line 848. The address valid signal line 848 is described below in more detail with reference to the fall-through blocks enable signals. The output of the buffer/driver 812 is coupled to the out_sig output pad 817 which is connected to the signal processor 300 via the linear out signal line 270 (FIGS. 4 and 5).

As shown in FIG. 7, a first input to the comparator 822 is provided via the input pad 802. A second input to the comparator 822 is provided via a threshold voltage ($V_{TH}$) input line 804 which is common to all modules in the system. If the detection element signal amplitude has a voltage that is lower than the threshold voltage, the event is not recorded. However, if the detection-element-signal amplitude is greater than the threshold ($V_{TH}$), the comparator 822 asserts its output (preferably by asserting a logical high value at its output) to set the corresponding latch 824. The signal remains recorded in the event latch 824 until it is processed and reset by the signal processor 300 as described below in more detail.

The AND gates 826, 828 serve two different timing functions. The AND gate 826 is used to ensure that the pulse generated by a detection element 212 is allowed to stabilize within the peak detector 820 (FIG. 7) associated with that detection element 212 before the valid signal is generated. The logical one is inverted before it is input to the AND gate 826, which causes the output of the AND gate to transition to a logical low value. The AND gate 826 output will continue to be maintained at a logical low value until the pulse received by the input 802 transitions below the threshold voltage. The AND gate 826 therefore prevents the output of the event latch 824 from passing though it to the AND gate 828 input until the pulse returns to a level below the threshold voltage. This delay ensures that the peak detector 820 is allowed to stabilize before a hit is passed on to the fall-through block 830. This ensures that the analog signal generated by the peak detector 820 via out_sig pad 817 corresponds to the peak amplitude of the pulse.

The AND gate 828 is used in conjunction with the fall-through block 830 to facilitate the fall-through scheme described above. As described below in more detail, the AND gate 828 prevents a detection element 212 which receives a hit from interrupting the fall-through process until the detection element is scanned by the fall-through circuit. The AND gate 828, together with the fall-through blocks, ensures that every event latch 824 is scanned in sequential order and that every detection element has an equal opportunity to be serviced by the signal processor 300.

As described above with reference to FIG. 5A when the "advance" signal 258 is asserted on advance input pad 842, the scanned event latch 824 is reset via reset line 844. As shown in FIG. 7, the reset line 844 of the enabled latch 824 is coupled to the priority-select/fall-through block 830. When a selected block 830 receives an advance signal 842, the block 830 resets the latch 824 via the reset line 844.

The fall-through blocks include "enable" outputs which are coupled to a plurality of address encoders (i.e., 832, 870, 890, etc.). An enable output of a selected fall-through block is asserted whenever the event latch 824 which is coupled to the selected priority select block contains an event and the selected priority select block is currently being scanned (i.e., the fall-through process has reached the selected priority select block). The enable outputs thereby cause one of the address encoders (e.g., 832) to present an address on an internal address bus 846 which is indicative of the selected detection element 212 containing a valid hit. A valid address signal 848 is then asserted which causes an analog switch 850 to close. The detection element address is then asserted on the detection element address bus 262 and transmitted to the signal processor 300.

As described above with reference to FIGS. 5–7, each detection module 206 has an analog ASIC 700 which amplifies the analog signals produced by the detection elements 212 and which compares the analog signals with an event threshold voltage which is common to all of the detection modules 206. The event threshold voltage is preferably established above noise level. When the analog signal produced by a detection element 212 exceeds the event threshold voltage and that detection element is "addressed" via the fall-through scheme as described above, the digital ASIC 800 generates a valid signal 260 which informs the computer signal processor 300 that at least one detection element 212 has received a hit requiring processing. The digital ASIC 800 takes control of the linear and address busses and outputs both the address of the detection element 212 and the magnitude of the amplified signal. The ASICs 700, 800 clear the flag and the linear signal produced by the addressed detection element 212 once the signal processor reads and processes the event. As described below in more detail, the signal processor 300 indicates when it has processed an event by asserting the "advance" signal via the advance signal line 258.

Thus, the gamma-ray detector 200 and, more specifically, the module board 208 appears to the signal processor 300 as a very simple analog/digital input device comprising an array of detectors which produce pulse-height and address information and which store this information until a read completion acknowledgment (via the advance signal 258) is provided by the signal processor 300. When the signal processor 300 has completed processing a detection element's address and reading the element's linear signal, the system generates an advance signal 258, thus allowing the next pending detection element to be addressed. The next element in the detection module array which has a hit pending will generate its address, its analog signal, and a valid flag. The signal processor 300 is thereby freed of the time-intensive task of polling each detection element 212, including detection elements which do not have pending hits. In fact, using the fall-through scheme described above with reference to FIGS. 5–7, the addressing of detection elements occurs independently of the processing performed by the signal processor 300. The signal processor 300 simply pulses its advance signal line 258 when it has read the detection element event data. As shown in FIG. 2, the signal processor 300 is housed on a circuit board that interfaces with the data acquisition computer 400. All communication between the signal processor 300 and the detector 200 occurs through the communications links 202 and 203.

Signal Processor 300

The signal processor 300 acquires data from the gamma-ray detector 200, normalizes and formats the data, and stores it in memory blocks for access by the data acquisition computer 400. In addition, the signal processor 300 provides the bias voltage for the detector 200 and provides the event threshold voltage that is used by the detection module 206 for discriminating valid gamma-ray pulses.

Figure 8:
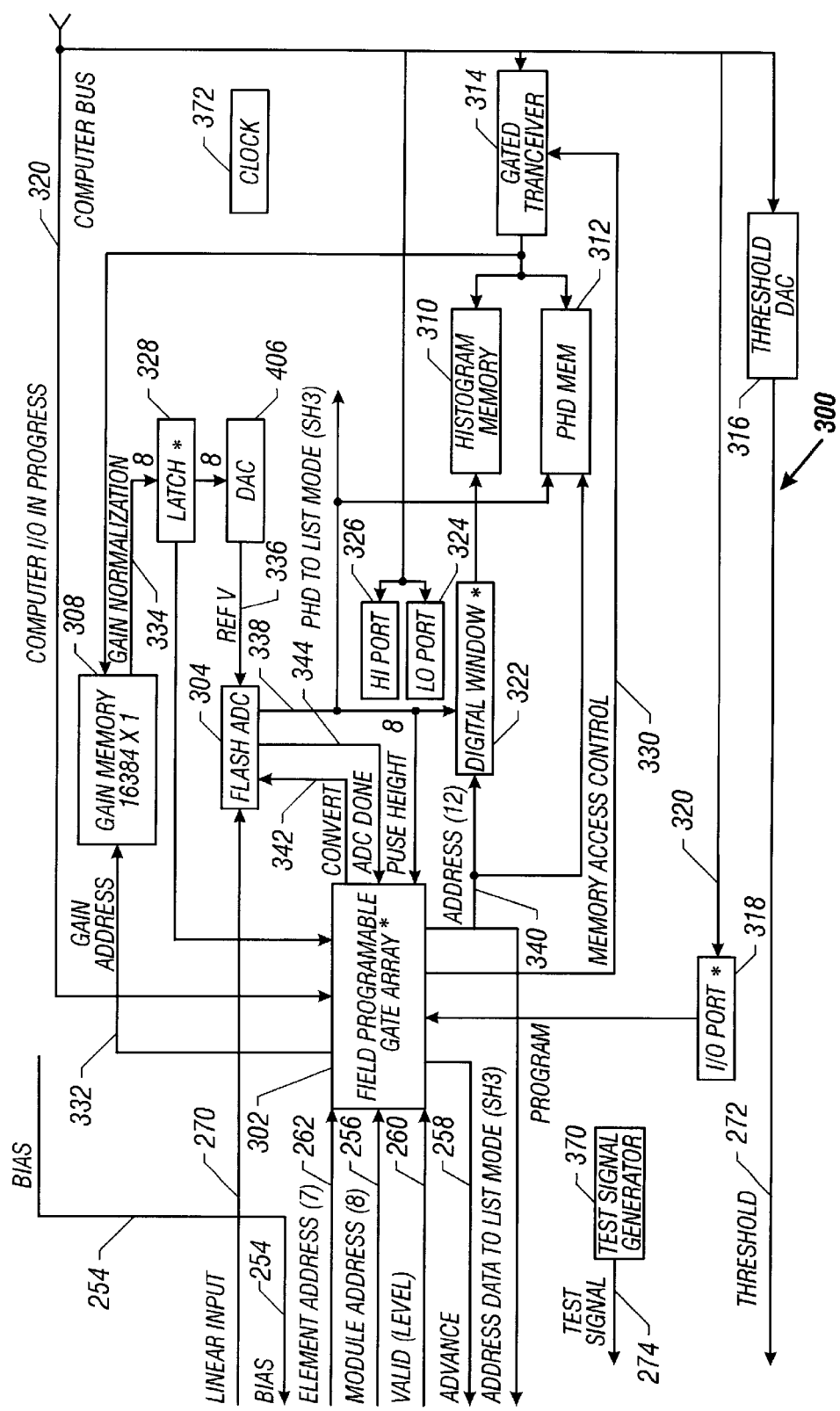
FIG. 8 shows a functional block diagram of the signal processor shown in FIG. 2.

FIG. 8 is a functional block diagram of the signal processor 300. The signal processor 300 preferably comprises a field programmable gate array (FPGA) 302; a flash analog-to-digital converter (ADC) 304; a fast digital-to-analog converter (DAC) 406 used for gain normalization; a threshold DAC 316 for setting the event threshold voltage; an input/output port 318 for communicating with the data acquisition computer 400; a gated transceiver 314; a digital window block 322, having a low port 324 and a high port 326; a latch 328; a test signal generator 370; a one-millisecond clock 372; and a bias voltage supply 254. As described below in more detail, the signal processor 300 also includes random access memory (RAM) which is allocated into several blocks: a gain memory block 308, a histogram memory block 310, and a pulse-height distribution memory block 312 which are named for the type of information stored therein. As described below in more detail with reference to FIG. 9, the signal processor 300 also includes two "ping-pong" buffers 346, 348, which store addresses used in the "streaming mode" of data storage.

All communication signals and power between the signal processor 300 and the module board are via communications links 202 and 203. For example, as shown in FIG. 8, the linear input line 270 is connected to the linear outputs of all detection modules 206 via analog communications link 203. The address inputs to the FPGA 302 are provided via address lines 256 and 262; the valid line is coupled to the valid signal line 260; the advance signal is provided over the advance signal line 258; the threshold voltage is transmitted over the threshold signal line 272; the test signals are provided on test signal lines 274; and the bias voltage is provided over the bias signal line 254, all via the analog link 203.

The FPGA 302 allows the functions of the signal processor 300 to be controllable via software. Upon initialization, the data acquisition computer 400 transmits configuration information to the signal processor 300 via the parallel input/output port 318. This configuration information designates the mode of data acquisition. For example, the signal processor 300 can configure the FPGA 302 to store event data which exceeds a software controlled threshold voltage in the histogram memory block 310. Alternatively, several pulse-height windows can be specified and a separate histogram can be accumulated in the histogram memory block 310 for each window. Additionally, a pulse-height distribution or spectrum received from each detection element 212 can be stored in the pulse-height memory block 312. Each of these modes can be separately specified upon initialization of the FPGA 302.

When the valid signal line 260 becomes true, the detection element address is read from the address lines 256, 262. This address is used to address a memory location containing the gain normalization factor for the element. This information is transferred to the DAC 406 that outputs a voltage proportional to the element gain. The voltage output by the DAC 406 is used by the ADC 304 in normalizing and converting the analog signal produced by the selected processing channel and provided on line 270.

The element address is also used to map the pulse-height amplitude into the histogram memory block 310 or, alternately, into the pulse-height distribution memory block 312. During an initial measurement, the gain normalization factors are set to unity and an isotopic source is used to measure the responses of the individual elements. These responses are then analyzed by the host computer to obtain the gain factors that will be used during imaging. In this way variances in element responses are eliminated, thus greatly improving image quality. When the event has been acquired, normalized, and stored, an advance signal is generated on line 258 which allows the gamma-ray detector 200 to advance to the next detection element that has a valid hit.

As described above, one important function performed by the signal processor 300 is detection-element-gain normalization. The signal processor uses the gain memory block 308 to perform this gain normalization function. The gain memory block 308 contains a gain normalization factor for each of the detection elements in the gamma-ray detector 200. In the preferred embodiment, there are as many as 256 detection modules 206 and sixty-four detection elements 212 per module. Each pulse-height distribution comprises 128 channels with a depth of two bytes. Therefore, in that example, the gain memory block 308 has 256×64×128×2, or 4,194,304 memory byte locations. When an event occurs, the gain memory 308 is addressed and the data is transferred to the gain normalization DAC 406. This in turn controls the instantaneous full-scale range of the ADC 304. The output of the ADC 304 is thus "gain normalized." The ADC "done" signal 344 causes the data storage operation to proceed.

The gain normalization factors are initially obtained by first setting the factors to unity. The signal processor 300 then accumulates a pulse-height distribution of each detection element in the pulse-height memory block 312. The pulse-height distribution is analyzed by the data acquisition computer 400 to obtain the relative gain for each element, a number proportional to this value is stored as a gain normalization factor for each detection element in the gain memory block 308. The gain normalization factors thereby obtained are used to normalize the analog signals subsequently received from each detection element 212 during data acquisition.

In pulse-height mode, the element addresses and the ADC output are used to address the pulse-height memory block 312 via address lines 340 and output lines 338 in building a pulse-height spectrum of each detection element 212. Thus, each element address is associated with a 128-location histogram. The upper seven bits of the ADC specify the "addresses" of these 128 locations. Each location in the histogram is incremented by one when its address appears on the ADC. More than one byte of memory at each location can be specified for improving statistical accuracy. Thus, the pulse-height memory 312 accumulates a pulse-height spectrum for each of the detection elements 212 in the gamma-ray detector 200. This spectrum can be analyzed by the data acquisition computer 400 by accessing the pulse-height memory 312.

In the image-collection modes, each detection element address is four bytes of memory deep and is incremented by one each time that address is presented on the address lines and the ADC output is of the proper amplitude. Thus, histograms of the incoming data can be created according to gamma-ray energy detected. As shown in FIG. 8, the addresses and the event amplitudes are presented via the address signal lines 340 and 338 to the digital window block 322. The digital window block has a high port 326 and a low port 324. The data acquisition computer 400 establishes the values provided to these ports by writing via the computer bus 320 a low and high amplitude value into the low and high ports 324, 326. The output of the ADC 304 is compared with the value stored in the low and high ports 324, 326. If the value on the amplitude lines 338 falls between the low and high values stored in the digital window's low and high ports 324, 326, the element address provided on address lines 340 is used to address the histogram memory 310. The value in the histogram memory 310 at the element address is incremented by one and rewritten at that address.

In "list" mode, each event is "time-tagged." Address information is combined with the eight bits from the ADC and three bits from a clock and placed in one of a ping-pong memory buffer pair. These buffers are sized to allow easy data transfer at high rates of data acquisition. When a buffer fills, data transfer is switched to the other buffer and an interrupt is generated which sets up a DMA transfer of the full buffer to a hard disk optionally coupled to either the data acquisition computer 400 or the image processing computer system 450. An output from a port will force flushing of the buffers at the termination of data acquisition.

For 256 modules addressable via eight address lines in the gamma-ray detector 200, each image histogram requires a block of 65,536 bytes of memory (256×64×4). The signal processor employs dual-ported memory so that both the FPGA 302 and the data acquisition computer 400 CPU can access the gain memory simultaneously.

Once the memories 310, 312 are written with detection element data, the FPGA 302 asserts the advance signal over advance signal line 258 which allows the next event to be presented on the event address lines 256, 262 and the linear input line 270. As described above with reference to FIGS.

5–7, the detection modules 206 are sequentially scanned until a module is found having a valid hit. The signal processor 300 reads the valid hit address and linear data. In the preferred embodiment, it takes approximately 2.5 microseconds to scan through all of the detection modules 206 when there is no valid hit, and it takes approximately 2 microseconds to process each detector element hit. At approximately 220,000 counts per second, the signal processor 300 will read an average of one data point per entire scan, and its maximum read rate is approximately 500,000 counts per second.

The imaging system 450 can produce live displays of gamma-ray pulse-height distributions or histograms of events which occur between pre-defined pulse-height levels. In addition, the data acquisition computer 400 can perform diagnostic functions based on the data in the memory blocks 310, 312. For example, in a preliminary measurement, the imager is exposed to a uniform field of radiation from the isotope to be used in the imaging. The data rate is recorded for each element in the system, and the relative count rate in each element is used to obtain a detection efficiency factor for that element. Subsequent analysis of the image employs these factors to correct incidental variances in element detection efficiencies.

As shown in FIG. 8, the signal processor 300 also includes a threshold DAC 316 which allows the threshold voltage provided to the detection modules 206 over threshold voltage line 272 to be adjusted under software control. The input to the threshold DAC 316 is provided via the computer bus 320.

Figure 9:
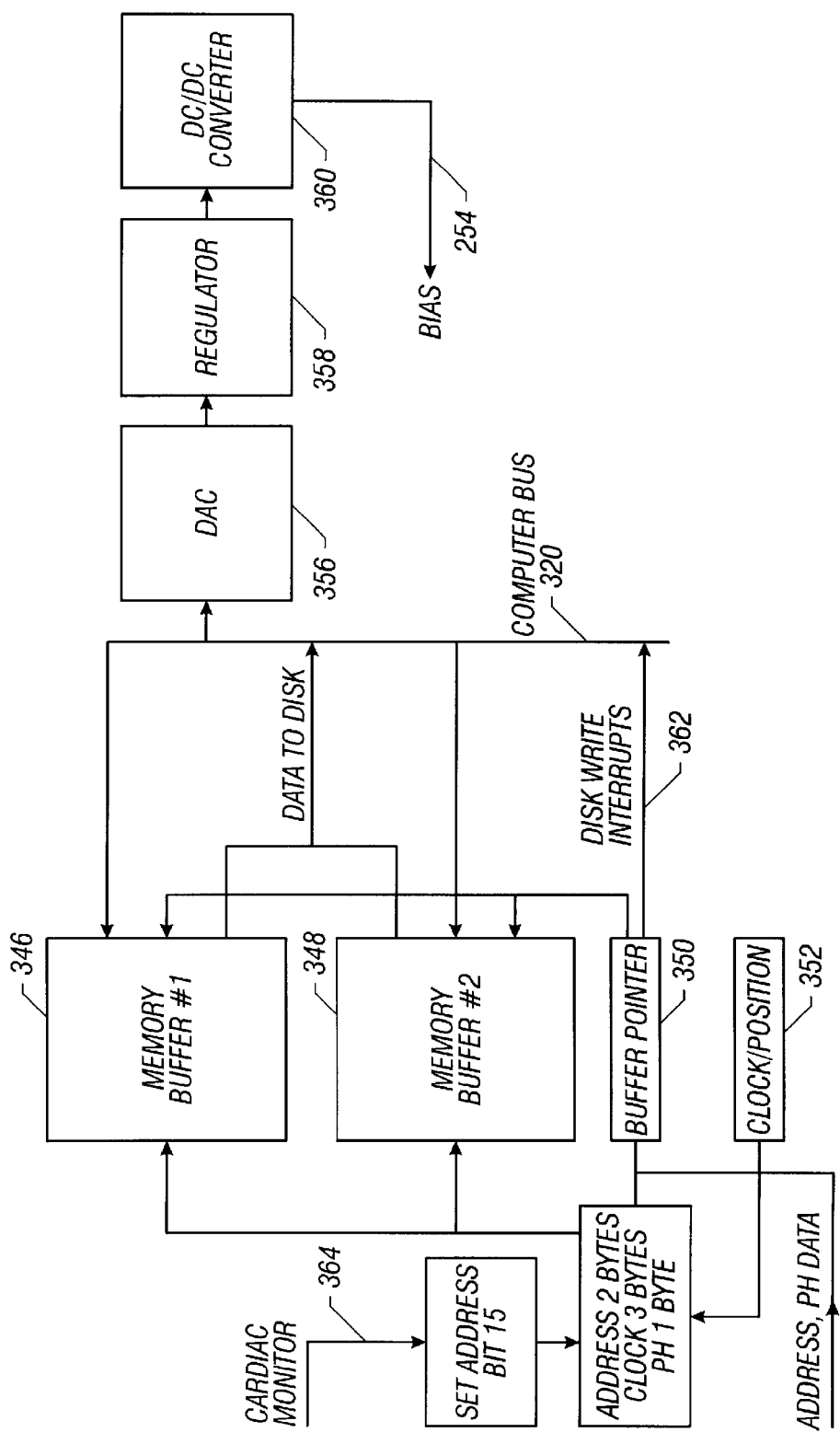
FIG. 9 shows additional details of the signal processor of FIG. 8.

In the preferred embodiment, the signal processor 300 also includes the blocks shown in FIG. 9. The signal processor 300 includes two memory address buffers 346, 348, a buffer pointer 350, and a 1-millisecond clock 352. Using the hardware shown in FIG. 9, the signal processor 300 can store address information in the memory address buffers 346, 348, in addition to creating histograms and storing histogram data in the histogram memory block 310 as described above. The address information is stored within the memory address buffers 346, 348 together with timing information generated by the clock 352. When the first memory buffer 346 becomes full, the addresses are routed by the buffer pointer 350 to the second memory buffer 348. When the first buffer 346 becomes full, the buffer pointer 350 also generates a disk write interrupt signal to the data acquisition computer 400 via the control line 362. As shown in FIG. 9, the control line 362 is coupled with the computer bus 320. When the buffer pointer asserts the interrupt signal on the control line 362, the data acquisition computer 400 begins executing a first interrupt routine to transfer the data from the first memory buffer 346 to a data disk (e.g., data storage device 614, FIG. 1). When the second memory buffer 348 becomes full, the buffer pointer 350 generates a second disk write interrupt which causes the data acquisition computer 400 to execute a second interrupt routine to transfer the data from the second buffer 348 to the data disk. Address information is subsequently loaded into the first buffer 346. This "streaming mode" of storage of address and timing information is controlled by the data acquisition computer 400 via software executing on the CPU.

To synchronize the address and data with the occurrence of external events, the signal processor 300 facilitates tagging the event with the address information stored in the memory address buffers 346, 348. For example, to synchronize the addresses stored in the memory buffers 346, 348 with an event such as a heart contraction, an input signal from a heart monitoring sensor is provided. The logic level input signal is provided over signal line 364. When an external event occurs, the signal line 364 is asserted, which causes a special tag to be inserted within the address data stream input into the buffers 346, 348. For example, an event can cause one of the address bits to be set or cleared and can thus be used as a flag. When the data is processed into time divisions, the tag time events will allow the data to be subdivided into phased time slices. In an alternative embodiment, memory buffers 346, 348 shown in FIG. 9 can accommodate address, pulse-height data, and timing information. Such streaming data can then be read back from the hard disk and sorted into time bins related to the external event flag. Thus it is possible to form a time history of the contractions of the heart or other repetitive occurrences. /Alternatively, the clock information can be replaced with pulses from an external position encoder that will allow position-dependent images to be accumulated for tomographic applications.

The DAC 356 works together with the regulator 358 and the DC/DC converter 360 to provide a regulated voltage source for the bias voltage 254. The input to the DAC 356 is provided via software control over the computer bus 320. A fraction of the converter output voltage is used as a comparison input to a high-gain operational amplifier. The amplifier controls the drive signal to the converter to maintain the operating bias at the desired value.

When an event occurs, the address of the detection element 212 which caused the event is used to address the gain memory block 308 via the gain address bus lines 332. In the illustrated embodiment, the FPGA 302 combines the module address bus 356 with the detection element address bus 262 to produce the gain address bus 332. As described above, the FPGA 302 treats the module address as the most significant address bits and the element address as the least significant address bits. When the gain memory block 308 is addressed by the FPGA 302 via the gain address lines 332, the pre-calculated gain normalization factor for the pending detection element 212 is presented on the gain normalization signal lines 334. The pre-stored gain normalization factor for the pending detection element 212 is then latched into the gain normalization latch 328. In the illustrated embodiment, the signal processor 300 uses an 8-bit DAC 406 which accepts the 8-bit gain normalization factor from the latch 328. When the selected gain normalization factor is latched into the latch 328, an analog reference value is produced by the DAC 406 corresponding to the 8-bit gain normalization factor. The gain reference voltage is output on reference voltage line 336, which is coupled to the flash ADC 304. The reference output voltage produced by the DAC 406 is used as a reference to the flash ADC 304. The input voltage to the flash ADC 304 is provided from the linear output line 270 of the detection module board 208. Because the flash ADC 304 is a ratio-metric type analog-to-digital converter, the output of the ADC 304 is proportional to the ratio of the input signal received on the linear input line 270 and the reference voltage provided by the DAC 406 via reference voltage line 336. Thus, the flash ADC 304 produces a digital representation of the amplitude of the linear input signal generated by the detection element (which received the hit) modified by the gain normalization factor stored in the gain memory 308 (for that detection element 212). The ADC 304 therefore produces an 8-bit output on amplitude line 338 which is independent of particular gain variations in each of the detection elements 212 and variations in the corresponding amplification and conditioning circuitry.

The FPGA 302 waits a short time for the gating transient of the latch 328 and the DAC 406 output to settle before issuing a convert signal to the flash ADC 304. The convert signal is provided over convert signal line 342 and causes the flash ADC 304 to generate a digital output on the amplitude line 338. The flash ADC 304 performs the analog-to-digital conversion in approximately 50 nanoseconds or less, and the total conversion time from the assertion of the convert signal on signal line 342 to the generation of an output on amplitude lines 338 is approximately 300 nanoseconds. The flash ADC 304 asserts an ADC done signal over the signal line 344 to inform the FPGA 302 when the conversion is completed. When the ADC done signal is asserted on signal line 344, the FPGA 302 asserts the advance signal on advance signal line 258 which frees the active detection module 206 to proceed with finding the next pending detection element event. The histogram memory 310 can be updated while the processing of the next detection element event is initiated.

Data Acquisition Computer

The data acquisition computer 400 includes hardware and software which communicate with the signal processor 300 and with the image processing computer system 450. The data acquisition computer 400 controls acquisition and processing of data received from the array of detection modules 206, produces image data based upon the event data in a format that is compatible with existing imaging cameras, and transmits that data to the image processing computer system 450. The data acquisition computer 400 also provides a mechanism for maintaining detection element event histograms and pulse-height distribution data and can produce images in a standard format to allow the images to be displayed using commercially available imaging systems for the image processing computer 450. For example, in one preferred embodiment, the data acquisition computer 400 delivers image histograms to an image-processing computer over a fast data link. In a second embodiment the relative location of each event and the signal amplitude are transmitted to the image processing computer via a parallel link. In this later embodiment the image processing computer would assume the task of producing histograms.

Images can be time-tagged at any desired rate that can be resolved by the clock. In one preferred embodiment the data are tagged at a rate of 30 frames per second. Therefore, if data is collected at approximately 300,000 counts per second, each time-tagged frame contains approximately 10,000 data points.

The data acquisition computer 400, together with the signal processor 300, increases the flexibility and reduces the cost of the detector 200 by performing detection-element-gain and detection-element-efficiency normalization functions. This benefit results from less stringent requirements on the quality of the detection elements and from eliminating the need for matching the gains of the detection-element/amplification/peak-detection strings. The data acquisition computer 400 analyzes the relative efficiency of each detection element 212 and performs a normalization function on the received data to ensure that a uniform radiation exposure produces an image having a uniform intensity (i.e., equally irradiated detection elements produce the same shade of gray for every pixel). Thus, after initialization, the signal processor 300 and data acquisition computer 400 ensure that, when equally irradiated, each detection element 212 produces an identically displayed response which is independent of the actual response produced by the detection element 212. This normalization feature reduces the costs associated with producing detection elements 212 and detection modules 206 having uniform response and gain characteristics. This feature eliminates the need to adjust the gains of each detection element 212 and its associated amplification and signal conditioning circuitry. This feature also allows improved energy resolution of each detection element 212 and improved rejection of Compton-scattered events. It also improves the long term stability of the imaging system. These features are achieved without a significant reduction of data throughput: total count rates of 500,000 counts per second can be processed by the present data acquisition computer 400.

The signal processor 300 and data acquisition computer 400 also provide increased flexibility by allowing functions to be changed under software control, thereby avoiding costly board redesigns when additional functionality is required or desired.

Image Processing Computer System

The image processing computer system 450 provides an interface with the operator, governs data acquisition modes, receives image data from the data acquisition computer 400, displays images in real time on the display 604, and communicates with display and readout devices. It also provides a facility for adjusting operational parameters, such as, the gamma-ray energy bounds and calibration parameters used by the system. The communication with the data acquisition computer 400 is via a standard interface such as Ethernet or SCSI-2 using a data protocol preferred by the particular image processing computer system 450 being used. The image processing computer system provides image display, rotation, slicing, region-of-interest highlighting, etc. under operator control.

As shown in FIG. 2, the image processing computer system 450 can also display images on any of the other display devices coupled to it. This system includes both software and hardware to control the input and output devices shown in FIG. 2.

Thus, a nuclear medicine imaging system has been described wherein the imaging system includes an imaging head 200, signal processor 300, and a data acquisition computer 400. The imaging head includes an array of closely-packed detection modules. Each detection module comprises an array of semiconductor detection elements mounted to a circuit carrier, wherein the circuit carrier includes circuitry to condition and process the signals generated by the detection elements and to prepare the processed signals for further processing by the signal processor. The imaging system formulates images based upon the processed signals and displays the formulated images on a display. The detection modules preferably comprise cadmium-zinc-telluride material. The address of each detection module and element is provided to the signal processor when the detection element absorbs a gamma ray of energy greater that a threshold controlled by the signal processor (a valid hit). The detection modules employ a fall-through scheme to automatically read only those detection elements, in sequence, that have received a valid hit and to produce the address of those elements and the magnitude of the absorbed photon. The signal processor performs diagnostics, gain normalization, response efficiency normalization, and data acquisition functions. The imaging system displays images based upon the signals generated by the detection elements.

A number of embodiments of the present invention have been described. Nevertheless, it will be understood that various modifications may be made without departing from the spirit and scope of the invention. For example, other buttable shapes could be used for the detection modules 206, such as triangular, rectangular or hexagonal. Similarly, the detection elements 212 could have other shapes besides square. Also, as described above, the two analog ASICs of each detection module can be combined into a single ASIC. Similarly, both the digital and analog functions can be implemented using one ASIC. In addition, the method of gain normalization could be performed completely in software after the analog values are converted to digital. Accordingly, it is to be understood that the invention is not to be limited by the specific illustrated embodiments, but only by the scope of the appended claims.

What is claimed is:

1. A modular radiation detection device for incident gamma radiation having a first frequency range, comprising:
a plurality of modules, each module including:
a down-conversion material, the down-conversion material emitting photons in a frequency range less than that of the first frequency range upon illumination by the incident gamma radiation;
an array of semiconductor photodetector elements positioned in line with the downconversion material, each photodetector element having a photodetector active area configured so as to receive a substantial portion of the photons of the second frequency range, providing an output signal when illuminated by the emitted light; and
an integrated circuit having an input from the output signals of said array of photodetectors; and
wherein the modules are all-side buttable.

2. The detection device of claim 1, further comprising a collimator to receive and collimate the incident gamma radiation having a first frequency range.

3. The detection device of claim 2, wherein said collimator includes a parallel array of holes having a predetermined shape.

4. The detection device of claim 3, wherein said hole shape is hexagonal.

5. The detection device of claim 3, wherein said hole shape is square.

6. The detection device of claim 3, wherein the down-conversion material is formed of an array of crystals for each of the plurality of modules.

7. The detection device of claim 6, wherein the crystals in the array are each separated by a layer of a substantially reflective material.

8. The detection device of claim 7, wherein the collimator holes are separated by septal walls, and wherein at least a portion of the septal walls of the collimator are substantially aligned with the substantially reflective material.

9. The detection device of claim 7, wherein at least a portion of the array of semiconductor photodetector elements are aligned with the substantially reflective material.

10. The detection device of claim 1, wherein said down-conversion material includes CsI.

11. The detection device of claim 10, wherein the CsI is activated with thallium.

12. The detection device of claim 10, wherein the CsI has a thickness in the range of a few millimeters to several centimeters.

13. The detection device of claim 12, wherein the CsI has a thickness of about 5 mm.

14. The detection device of claim 1, wherein the integrated circuit includes a separate input for each photodetector element.

15. The detection device of claim 1, wherein the down-conversion material is formed of one crystal for each of the plurality modules.

16. The detection device of claim 1, wherein the semiconductor photodetector elements include CZT elements.

17. The detection device of claim 16, wherein the semiconductor photodetector elements further comprise electrodes for providing an electric field across the CZT elements, at least one of the electrodes being transparent to photons having frequencies in the second frequency range.

18. The detection device of claim 1, wherein the semiconductor photodetector elements include silicon PIN diodes and wherein the semiconductor photodetector elements further comprise electrodes for providing an electric field across the PIN diodes, at least one of the electrodes being transparent to photons having frequencies in the second frequency range.

19. The detection device of claim 1, wherein the semiconductor photodetector elements include mercuric iodide elements and wherein the semiconductor photodetector elements further comprise electrodes for providing an electric field across the mercuric iodide elements, at least one of the electrodes being transparent to photons having frequencies in the second frequency range.

20. The detection device of claim 1, wherein the semiconductor photodetector elements include gallium arsenide elements and wherein the semiconductor photodetector elements further comprise electrodes for providing an electric field across the gallium arsenide elements, at least one of the electrodes being transparent to photons having frequencies in the second frequency range.

21. The detection device of claim 1, wherein the plurality of modules is of a size and shape appropriate to image an organ of the human body.

22. The detection device of claim 1, wherein each module is square and the plurality of modules forms an N×M array.

23. The detection device of claim 1, wherein a total thickness of the device is less than about 3 inches.

24. The detection device of claim 23, wherein a total thickness of the device is about 2 inches.

25. The detection device of claim 1, further comprising a video monitor.

26. The detection device of claim 1, further comprising a housing surrounding the plurality of modules, wherein said housing includes a cooling system to control a temperature within the detection device.

27. The detection device of claim 26, wherein said housing seals the modules from the environment.

* * * * *